Figure 1:
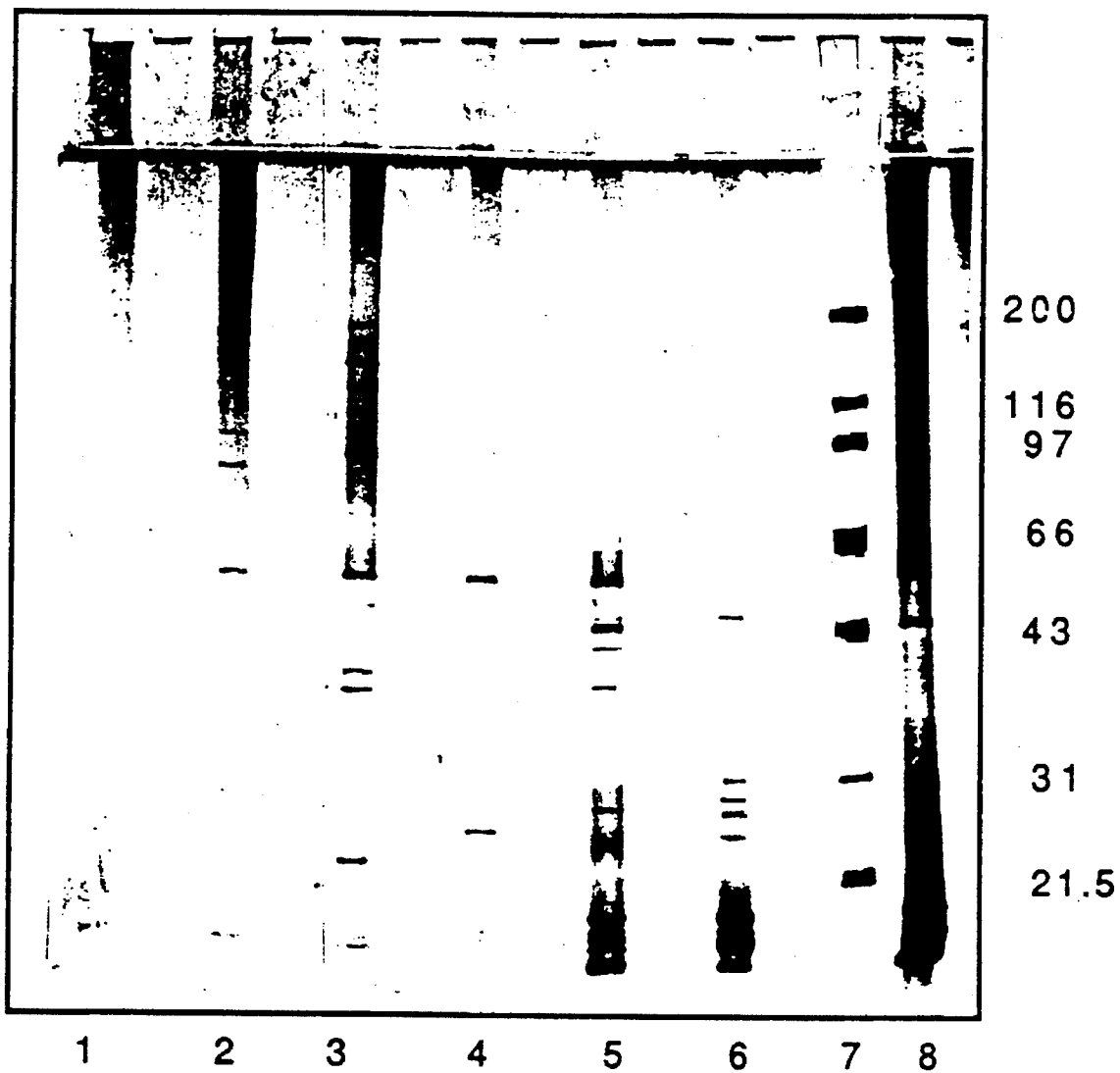

United States Patent [19]

Sharp et al.

[11] Patent Number: 5,525,508
[45] Date of Patent: Jun. 11, 1996

[54] HAEMONCHUS CONTORTUS VACCINE

[75] Inventors: Phillip J. Sharp, Glebe; Barry M. Wagland, Carlingford; Gary S. Cobon, Frenchs Forest, all of Australia

[73] Assignees: Biotech Australia Pty Limited, Roseville; Commonwealth and Industrial Research Organization, Campbell, both of Australia

[21] Appl. No.: 930,686

[22] PCT Filed: Feb. 5, 1992

[86] PCT No.: PCT/AU92/00040

§ 371 Date: Oct. 6, 1992

§ 102(e) Date: Oct. 6, 1992

[87] PCT Pub. No.: WO92/13889

PCT Pub. Date: Aug. 20, 1992

[30] Foreign Application Priority Data

Feb. 6, 1991 [AU] Australia ................................ PK4486

[51] Int. Cl.[6] ...................... A61K 39/002; C07K 14/44; C12N 15/30
[52] U.S. Cl. .................... 424/265.1; 424/184.1; 424/185.1; 424/266.1; 514/2; 435/69.3.; 435/172.3; 435/252.3; 530/350; 530/395; 530/403; 530/822; 530/412; 530/413; 530/416; 536/23.1; 536/23.4; 536/23.5
[58] Field of Search ..................... 530/350, 395, 530/403, 822, 825, 412–417; 424/88, 184.1, 185.1, 265.1, 266.1; 435/69.3; 172.3; 514/2; 536/23.1, 23.4, 23.5

[56] References Cited

FOREIGN PATENT DOCUMENTS

| 49035/90 | 11/1990 | Australia . |
| 89/00163 | 1/1989 | WIPO . |
| 90/03433 | 4/1990 | WIPO . |
| 9011086 | 10/1990 | WIPO . |

OTHER PUBLICATIONS

Bowie, A. V. et al. Science 247: 1306–1310 (1990).
Kumar, V. et al. Proc. Natl. Acad. Sci 87:1337–1341 (1990).
Ellis, R. W. In: Vaccines Plotkin & Mortimer Eds. W. B. Saunders Co., (1988) pp. 568–515.
Silberstein, O. S. et al. Science 227: 948–50 (1985).
Gold K. M. et al. Mol. Biochem. Parasitol 41: 187–196 (1980).
Young, R. A. et al. Proc. Natl. Acad. Sci. 80: 1194–1198 (1983).
Scopes, R. K. Protein Purfication: Principles and practice Springer–Velag (1987) pp. 221–235.
Gerard, C. et al. "Purification of Glycoproteins" Methods of Enzymology 182:529–534 (1990).
Kennedy, M. W. and Queshi F., "Stage-specific secreted antigens of the parasitic larval stages of the nematode Ascaris", Immunology, vol. 58, 1986, pp. 516–522.
Friedlander et al., "Immunological Aspects of Murine Infection With The Rat Nematode *Strongyloides ratti* Sandground, 1925, "Z Parasitenkd. 72: 493–509 (1986).
International Journal of Parasitology, vol. 15, No. 2, pp. 129–136, 1985, O'Donnell, Attempts To Probe The Antigens And Protective Immunogens Of Trichostrongylus, etc.

*Primary Examiner*—Hazel F. Sidberry
*Assistant Examiner*—Michael S. Tuscan
*Attorney, Agent, or Firm*—Foley & Lardner

[57] ABSTRACT

A substantially purified antigen derived from a first species of parasitic nematodes, which antigen is capable of providing protection to a host from parasitism by a second nematode species, which may be the same as or different from the first nematode species, following vaccination of the host with the antigen, characterized in that the antigen is proteinaceous, has a pI between 3.8 and 4.4, can be bound by lentil lectin and *Helix promatia* lectin and has a molecular weight of approximately 45 kD as determined by SDS-PAGE.

15 Claims, 18 Drawing Sheets

FIG. 7A

FIG. 7B

| | 604 | | 613 | | 622 | | 631 | | 640 | | 649 |
|---|---|---|---|---|---|---|---|---|---|---|---|
| GTC | GAG | ATG | GAT | CCA | ACA | ACT | GAC | GCC | AAA | TGT | GCT | GGT |
| Val | Glu | MET | Asp | Pro | Thr | Thr | Asp | Ala | Lys | Cys | Ala | Gly |
| | 658 | | 667 | | 676 | | 685 | | 694 | | 703 |
| TGC | GTT | AGC | GAA | GCC | CTT | TGC | CCG | CCA | TAC | ACT | CCC | CTT |
| Cys | Val | Ser | Glu | Ala | Leu | Cys | Pro | Pro | Tyr | Thr | Pro | Leu |
| | 712 | | 721 | | 730 | | 739 | | 748 | | 757 |
| CCA | ACT | ACC | TCA | ACC | ACA | CCG | AAG | CCA | ACA | ACA | ACC | GTT |
| Pro | Thr | Thr | Ser | Thr | Thr | Pro | Lys | Pro | Thr | Thr | Thr | Val |
| | 766 | | 775 | | 784 | | 793 | | 802 | | 811 |
| GGG | CCT | AAT | GCT | TCG | TGC | CCT | GAA | CTT | AAT | ACT | GAC | GAA |
| Gly | Pro | Asn | Ala | Ser | Cys | Pro | Glu | Leu | Asn | Thr | Asp | Glu |
| | 820 | | 829 | | 838 | | 847 | | 856 | | 865 |
| GCT | AGG | ATG | GTC | GAC | AAA | CAT | AAT | GAA | TAC | CGA | TCG | ATT | GCT | AAA |
| Ala | Arg | MET | Val | Asp | Lys | His | Asn | Glu | Tyr | Arg | Ser | Leu | Ile | Ala | Lys |
| | 874 | | 883 | | 892 | | 901 | | 910 | | 919 |
| GGG | CAA | AAG | GGT | CCT | CAA | GGA | TTC | CCA | GCC | AAG | GCT | AGA | ATG |
| Gly | Gln | Lys | Gly | Pro | Gln | Gly | Phe | Pro | Ala | Lys | Ala | Arg | MET |
| | 928 | | 937 | | 946 | | 955 | | 964 | | 973 |
| AAA | GTG | AAC | TAC | TGC | GAT | GTT | GAA | GCA | AAT | ATG | TGG | TCC | AAG | ACT |
| Lys | Val | Asn | Tyr | Cys | Asp | Val | Glu | Ala | Asn | MET | Trp | Ser | Lys | Thr |
| | 982 | | 991 | | 1000 | | 1009 | | 1018 | | 1027 |
| TGC | ACA | GGA | CTC | ACT | GCG | ATG | TTA | AAG | CGA | GGG | AAT | AAC | ATG |
| Cys | Thr | Gly | Leu | Thr | Ala | MET | Leu | Lys | Arg | Gly | Asn | Asn | MET |
| | 1036 | | 1045 | | 1054 | | 1063 | | 1072 | | 1081 |
| CAC | ATG | TCG | AAG | GCT | AAT | AAG | ACA | GAG | GCA | ATG | GAG | GCC | GTC |
| His | MET | Ser | Lys | Ala | Asn | Lys | Thr | Glu | Ala | MET | Glu | Ala | Val |
| | 1090 | | 1099 | | 1108 | | 1117 | | 1126 | | 1135 |
| GCA | GCC | TTC | GAT | TTA | CAA | TAT | GGC | GTA | CCT | GAG | AAT | AAC | GTC | TTC |
| Ala | Ala | Phe | Gly | Asp | Leu | Gln | Tyr | Gly | Val | Pro | Glu | Asn | Asn | Val | Phe |

| | | | | | | | | 1189 CAA TCG Gln Ser |
|---|---|---|---|---|---|---|---|---|

FROM FIG. 7B

```
                                                                        1189
    1144            1153            1162    1171            1180        CAA TCG
ACG ATG GTT TAC ACG ACT TTA AGT AAA TAC AGT CAG TTA GCG TGG             Gln Ser
Thr MET Val Tyr Thr Thr Leu Ser Lys Tyr Ser Gln Leu Ala Trp 1243
    1198            1207            1216    1225            1234        GTT GTG
AGC GAC AGA ATT GGT TGT GTA GTA CCT TGT TGG AGC TCA TGG ACG             Val Val
Ser Asp Arg Ile Gly Cys Val Val Pro Cys Trp Ser-Ser Trp Thr 1297
    1252            1261            1270    1279            1288        TAT GAC GTA
GTT TGT GAA TAC AAT CCC GGA GAC CTG CCT GGC GAG GCT ATC                 Tyr Asp Val
Val Cys Glu Tyr Asn Pro Gly Asp Leu Pro Gly Glu Ala Ile 1351
    1306            1315            1324    1333            1342        TGT AGC
GGA GAT CCC ACG AAA GAC GCC GAC CAG TGT GGC TGC ACC                     Cys Ser
Gly Asp Pro Thr Lys Asp Ala Asp Gln Cys Pro Gly Cys Thr 1360            1369            1378    1391        1400
AGA GAT GGC CTT TGC GTT GCT CCA TGA ACACTGGCGG CCGCTTAAG
Arg Asp Glu Gly Leu Cys Val Ala Pro >
```

FIG. 7C

FIG. 8A

```
pBTA963  10                19          28          37          46          55
 GAATTCGCGG CCGCTT >TCG GTG CTT CTG ACG CCA TCA TGC CTG AAA GCC GCG TTT
                    Ser Val Leu Leu Thr Pro Ser Cys Leu Lys Ala Ala Phe
         64          73          82          91         100         109
TGC CCC ACA TCG GAC AAT GGC ATG ACC GAT GAA ATT AGG CAG ATT TTC GTT GAT
Cys Pro Thr Ser Asp Asn Gly MET Thr Asp Glu Ile Arg Gln Ile Phe Val Asp
        118         127         136         145         154         163
AAG CAC AAT GAG TAT CGA TCT ATT ATT GCT AAA GGA CAG GCC AAG AAT AAA CTT
Lys His Asn Glu Tyr Arg Ser Ile Ile Ala Lys Gly Gln Ala Lys Asn Lys Leu
        172         181         190         199         208         217
GGA GGA TTC GCT CCG AAA GCA GCT CGA ATG TTG AAA GTG GGT TAC GAT TGC GAA
Gly Gly Phe Ala Pro Lys Ala Ala Arg MET Leu Lys Val Gly Tyr Asp Cys Glu
        226         235         244         253         262         271
GTT GAG GCA AAT ACG GCG GCA TAT GCA AAA GAG TGC AAG TTC GAA CAT GAT CCA
Val Glu Ala Asn Thr Ala Ala Tyr Ala Lys Glu Cys Lys Phe Glu His Asp Pro
        280         289         298         307         316         325
CCC GAG CAA AGG AAT TAT TGG GGG CAG AAC CTG TGG ATG CTA GGA GGG ACT AAT
Pro Glu Gln Arg Asn Tyr Trp Gly Gln Asn Leu Trp MET Leu Gly Gly Thr Asn
        334         343         352         361         370         379
TAC AGC AAG ACG GAA TCT GCA AAA TTA AGT GTC CAA GCT TGG TAC TGG GAA TTG
Tyr Ser Lys Thr Glu Ser Ala Lys Leu Ser Val Gln Ala Trp Tyr Trp Glu Leu
        388         397         406         415         424         433
AAG ATG TTT GGA GTG CCC GAT GAA AAT ATC CTG ACA ATG GAA GTC TTC GAT CGG
Lys MET Phe Gly Val Pro Asp Glu Asn Ile Leu Thr MET Glu Val Phe Asp Arg
        442         451         460         469         478         487
GGT GTT GGC CAC TAC ACA CAG GTA GCC TGG CAG TCT AGC GAC AAA ATC GGC TGC
Gly Val Gly His Tyr Thr Gln Val Ala Trp Gln Ser Ser Asp Lys Ile Gly Cys
        496         505         514         523         532         541
GCA GTT GAA TGG TGC CCA ACC ATG ACA CTT GTA GCA TGC GAG TAC AAC CCT GCA
Ala Val Glu Trp Cys Pro Thr MET Thr Leu Val Ala Cys Glu Tyr Asn Pro Ala
        550         559         568         577         586         595
GGA AAT AGG ATC AAT CAT TAT ATT TAC GAC ATC GGA GAT CCA TGC ACA ACT GAT
Gly Asn Arg Ile Asn His Tyr Ile Tyr Asp Ile Gly Asp Pro Cys Thr Thr Asp
```

TO FIG. 8B TO FIG. 8B

FIG. 8B

| | | | | | | | | | | | | | |
|---|---|---|---|---|---|---|---|---|---|---|---|---|---|
| FROM FIG. 8A | | | | | | | | | | | | | |
| GAA Glu | GAC Asp | 604 TGT Cys | CAA Gln | TGC Cys | 613 ACT Thr | GGC Gly | TGT Cys | 622 ACT Thr | AGT Ser | AAA Lys | 631 GAT Asp | GAG Glu | 640 GCC Ala | CTT Leu | TGT Cys | 649 ATT Ile |
| CCT Pro | CCA Pro | 658 GGA Gly | TAT Tyr | ACT Thr | 667 ACC Thr | GTC Val | ATG MET | 676 CCA Pro | CCG Pro | ACA Thr | 685 ACA Thr | GAG Glu | 694 CCT Pro | ACT Thr | ACA Thr | 703 ACA Thr |
| CCT Pro | AAA Lys | 712 ATA Ile | TAC Tyr | CAT His | 721 CCA Pro | GGT Gly | GGG Gly | 730 ATG MET | GGG Gly | AAT Asn | 739 GAG Glu | AAT Asn | 748 AAC Asn | GGA Gly | ATG MET | 757 ACA Thr |
| GAT Asp | GAA Glu | 766 GCT Ala | AGG Arg | CAG Gln | 775 ATG MET | TTC Phe | GTC Val | 784 GAC Asp | AAA Lys | CCT Pro | 793 AAT Asn | CAC His | TAT Tyr | 802 CGA Arg | TCC Ser | CTC Leu | 811 ATA Ile |
| GCT Ala | AAA Lys | 820 GGA Gly | CTA Leu | GCT Ala | 829 CAT His | AAT Asn | AAA Lys | 838 CTT Leu | GGA Gly | GGG Gly | 847 TTT Phe | GCT Ala | 856 AAA Lys | CCA Pro | GCT Ala | 865 AGA Arg |
| ATG MET | ATG MET | 874 AAA Lys | GTG Val | AGC Ser | 883 TAC Tyr | AAT Asn | TGC Cys | 892 GAA Glu | ATC Ile | GCG Ala | 901 GCG Ala | GAA Glu | AAT Asn | CGA Arg | GTG Val | 919 GCG Ala |
| AAG Lys | GAT Asp | 928 TGC Cys | ACG Thr | CTT Leu | 937 GGG Gly | TAC Tyr | AAC Asn | 946 TCT Ser | ACA Thr | CAA Gln | 955 CAA Gln | GTA Val | AAT Asn | CGA Arg | TGG Trp | 973 TAT Tyr |
| AAT Asn | GTA Val | 982 CAT His | TCA Ser | CTA Leu | 991 CTG Leu | CCG Pro | CAT His | 1000 ATT Ile | ATT Ile | CAT His | 1009 ACG Thr | AAG Lys | 1018 GCA Ala | GCA Ala | GCA Ala | 1027 AGT Ser |
| GTC Val | GAG Glu | 1036 GCC Ala | TGG Trp | TTC Phe | 1045 AAT Asn | GAA Glu | TAC Tyr | 1054 CAG Gln | CTA Leu | ACA Thr | 1063 GGT Gly | TAT Tyr | GCA Ala | CCT Pro | GAT Asp | 1081 AAC Asn |
| TTC Phe | AGT Ser | 1090 ATG MET | GAG Glu | GTT Val | 1099 TTC Phe | AAT Asn | CAA Gln | 1108 AAC Asn | GTA Val | ATA Ile | 1117 CAG Gln | GAA Glu | TAC Tyr | 1126 GCT Ala | CAG Gln | TTG Leu | 1135 GCG Ala |
| TO FIG. 8C | | | | | | | | | | | | | TO FIG. 8C | | | |

FIG. 8C

```
                                                              FROM FIG. 8B
FROM FIG. 8B
        1144            1153            1162            1171            1180            1189
TGG CAA TCG AGC AAC CAG ATT GGT TGT GGA ATT TTT TCT TGC TGG GGT GGC GCC
Trp Gln Ser Ser Asn Gln Ile Gly Cys Gly Ile Phe Ser Cys Trp Gly Gly Ala
        1198            1207            1216            1225            1234            1243
TCT ACA TTT GTG GCT TGC GAA TAC AAT CCT GGA AAC TTC ATC GGC GAA TTG
BSer Thr Phe Val Ala Cys Glu Tyr Asn Pro Gly Gly Asn Phe Ile Gly Glu Leu
        1252            1261            1270            1279            1288            1297
ATT TAT ACG ATG GGA GAT CCG TGC TCA ACT GAC GAA GAC TGT CAG TGC GCT GGT
Ile Tyr Thr MET Gly Asp Pro Cys Ser Thr Asp Glu Asp Cys Gln Cys Ala Gly
        1306            1315            1324            1333                  1349         1359
TGC GTC TGT AGC AGA GAT AAA GAT GAA GCA CTC TGT ATT GCT CCT TAA ATGCTTGTGC AATAAATCTT
Cys Val Cys Ser Arg Asp Lys Asp Glu Ala Leu Cys Ile Ala Pro

CAGTGAAAGA AAAGCGGCCG CGAATTC 1386
```

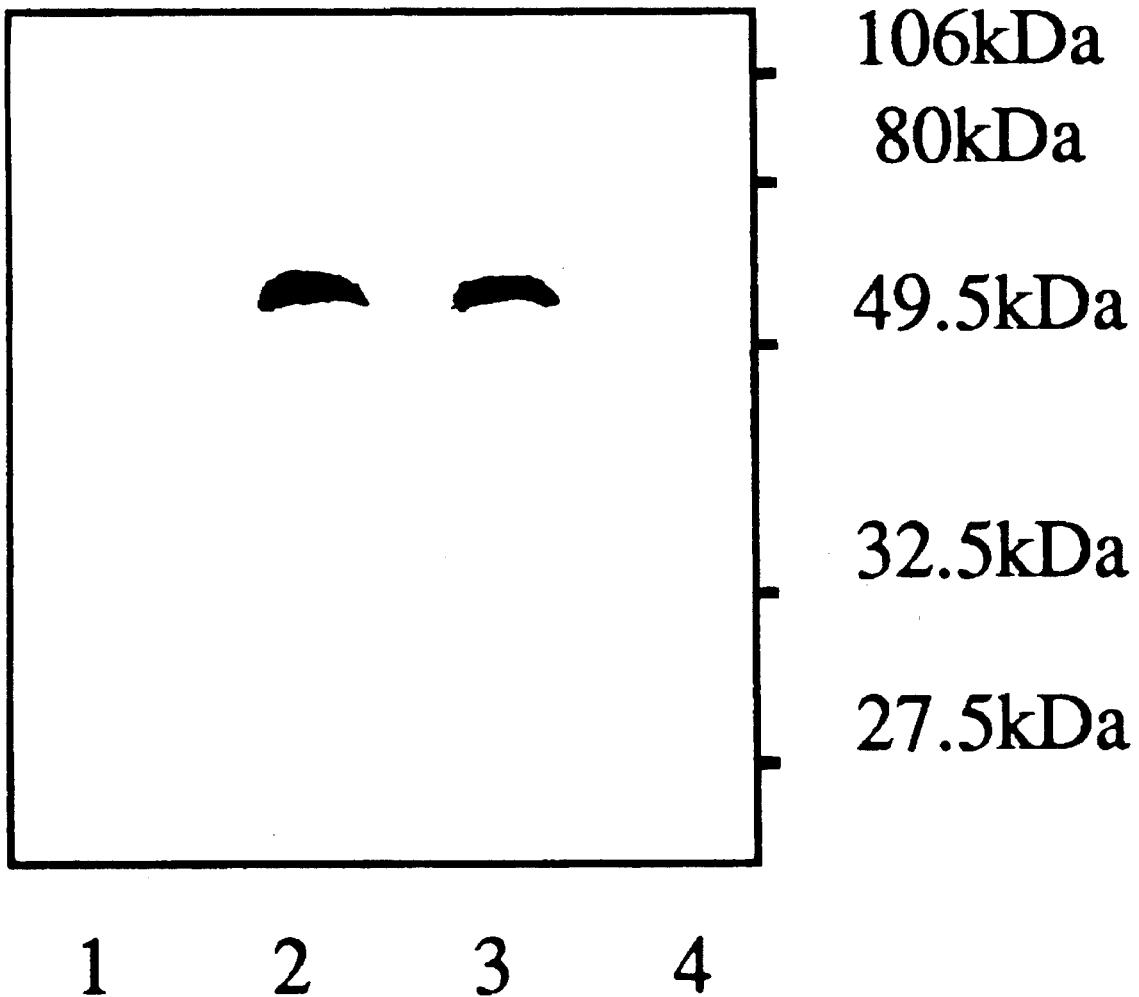
FIG. IIB

HAEMONCHUS CONTORTUS VACCINE

TECHNICAL FIELD

The invention relates to antigens which confer protective immunity against infection by parasitic nematodes.

The invention also relates to vaccines conferring protective immunity against infection by parasitic nematodes, and to antibodies conferring passive immunity to infection by parasitic nematodes.

BACKGROUND ART

Nematodes (nema - thread; oides - resembling), which are unsegmented roundworms with elongated, fusiform, or sac-like bodies covered with cuticle, are virtually ubiquitous in nature, inhabiting soil, water and plants, and are importantly involved in a wide range of animal and plant parasitic diseases.

The roundworm parasites of mammals belong to the phylum Nemathelminthes. The roundworms include the hookworm (e.g. *Necator americanus* and *Ancylostoma duodenale*), roundworm (e.g. the common roundworm *Ascaris lumbricoides*), whipworm (e.g. *Trichuris trichiura*), and the pinworm or threadworm (e.g. *Enterobius vermicularus*), as well as *Strongyloides stercoralis*, *Trichinella spiralis* (infection in man and pigs), and the filarial worm *Wuchereria bancrofti*. Other important roundworm parasites include *Ancylostoma caninum* (infections of man), *Strongylus vulgaris* (infections of horses), *Trichostrongylus colubriformis* (infections of sheep), *Haemonchus contortus* (infections of sheep and goats), *Ostertagia ostertagi* (infections of cattle), *Ascaris suum* (infections in pigs), *Toxascaris leonia* or *Uncinaria stenocephala* (infections of dogs), Toxocara spp (circulatory infections of man) and *Dirofilaria immitis* (circulatory infections of cats and dogs).

Even when symptom-free, parasitic worm infections are harmful to the host animal for a number of reasons; e.g. they deprive the host of food, injure organs or obstruct ducts, may elaborate substances toxic to the host, and provide a port of entry for other organisms. In other cases, the host may be a species raised for food and the parasite may be transmitted upon eating to infect the ingesting animal. It is highly desirable to eliminate such parasites as soon as they have been discovered.

More commonly, such infections are not symptom-free. Helminth infections of mammals, particularly by parasitic nematodes, are a source of great economic loss, especially of livestock and pets, e.g. sheep, cattle, horses, pigs, goats, dogs, cats and birds, especially poultry. These animals must be regularly treated with anthelminthic chemicals in order to keep such infections under control, or else the disease may result in anaemia, diarrohea, dehydration, loss of appetite, and even death.

The only currently available means for controlling helminth infections is with the use of anthelminthic chemicals, but these are only effective against resident worms present at the time of treatment. Therefore, treatment must be continuous since the animals are constantly exposed to infection; e.g. anthelminthic treatment with diethylcarbamazine is required every day or every other day most of the year to control *Dirofilaria immitis* or the dog heartworm. This is an expensive and labor intensive procedure. Due to the widespread use of anthelminthic chemicals, the worms may develop resistance and so new and more potent classes of chemicals must be developed. An alternative approach is clearly desirable.

The development of a vaccine against parasitic nematodes would overcome many of the drawbacks inherent in chemical treatment for the prevention and curing of helminthic infections. The protection would certainly last longer, only the vaccinated animal would be affected, and the problems of toxicity and persistence of residues would be minimized or avoided. Accordingly, there have been attempts, reported in the prior art, to develop such vaccines using parasitic nematodes; unfortunately, they have met with limited success and factors such as material availability and vaccine stability have precluded their large scale use.

These previous attempts are discussed in International Patent Application No. PCT/AU88/00239 (WO 89/00163) and PCT/AU89/00416 (WO 90/03433).

Recent advances in biotechnology and in particular recombinant DNA technology, realistically offer the opportunity to produce commercially-viable vaccines against a range of economically-important parasites of man and domestic animals. This approach would overcome many of the problems proposed to account for the lack of efficacy of killed vaccines using crude parasite preparations. For example, the vaccines produced by recombinant DNA techniques would not contain immunosuppressants or immunomodulators which may be found in crude extracts of parasitic nematode species. But it is necessary to first identify the antigens. Once identified and characterized, recombinant DNA technology could be used to construct microorganisms which synthesize those proteins or portions of the proteins containing protective epitopes and use the products synthesized by the recombinant organism in vaccines to protect animals from infection with the parasites.

In PCT/AU88/00239 it has been demonstrated that a recombinant DNA derived antigen shown to be nematode tropomyosin, gave 50% protection in sheep against *Haemonchus contortus* challenge. In PCT/AU89/00416 excretory/secretory antigens from adult *Trichostrongylus colubriformis* have been shown to give protection to vaccinated guinea pigs. For reasons which will become clear later in the specification, these antigens are different from the antigen identified in the current specification.

DESCRIPTION OF THE INVENTION

Definitions

The term "adjuvant" as used throughout the specification refers to an agent used to enhance the immune response of the immunised host to the immunising composition.

The term "parenteral" as used herein includes subcutaneous injections, intraperitoneal or intramuscular injection, or infusion techniques.

The term "homologue" refers to proteins or to DNA sequences coding for those proteins which are related in structure to a first protein or DNA sequence to such an extent that it is clear that the proteins are related in function. In the context of this invention, it is demonstrated that the DNA from *H. contortus* which codes for the antigen of the invention can be used in DNA hybridisation experiments to identify specific DNA sequences in other species of parasitic nematodes. The conditions under which the hybridisation experiments were carried out indicate that the related DNA sequences are at least 50% homologous in nucleotide sequence over 60 base pairs to that isolated from *H. contortus*. These related DNA segments code for antigens in those other species of parasitic nematodes which are also related in amino acid sequence to the protective antigen isolated from *H contortus*. It is contended that the related proteins will act as effective immunogens to protect animals from parasitism by the other species of parasites. These related DNA sequences are referred to as homologous genes and the related proteins are referred to as homologous antigens. Also, in the context of this invention, it has been demonstrated tht the protective antigen is a member of a gene family wherein the encoding polynucleotide and the gene product share an homology of the order of 50% over 60 nucleotides or 70% over 20 amino acids respectively with the encoding gene and protective antigen of this invention. These related genes and gene products are also homologues of this invention.

Homologues of the invention my also be generated in vitro as hereinafter described.

The term "derived" in the context of the antigens of the invention as used herein is intended to encompass antigen obtained by isolation from a parasitic nemanode life stage expressing the antigen, as well as antigen obtained by manipulation of and expression from nucleotide sequences prepared from a parasitic nematode life stage, including genomic DNA, mRNA, cDNA synthesized from mRNA and synthetic nucleotides prepared to have sequences corresponding to the antiget encoding sequences.

It is also intended to encompass synthetic peptide antigens prepared on the basis of the known amino acid sequences of the antigen as expressed by nematodes or cell lines expressing recombinant forms of the antigen.

Disclosure

It is preferable, if possible, to identify "novel" or "concealed" antigens i.e. components of the parasite which can act as effective and protective immunogens but which are not involved in naturally acquired immunity. To identify those components it is necessary to vaccinate the host with extracts from the parasite, identify fractions which give some protection, subfractionate the protective components using protein chemistry techniques, vaccinate animals with those subfractions and identify those subfractions which protect and continue with that process until a pure parasite component is used to vaccinate and protect the animal.

As much as possible, the natural host should be used in such experiments. As laboratory model animals are not the natural host for the parasite they are likely to be able to reject the parasite by mechanisms of which the natural host is incapable. Thus it is possible that antigens which protect laboratory animals against particular parasites may not be effective in the natural host of the parasite. This will be more likely to be the case in situations where the natural host develops immunity to the parasite very slowly.

The antigen characterised in the current work is derived from *Haemonchus contortus* but it is recognised that similar or related antigens, "homologues", could be identified from other species of parasitic nematode known to infect man or domestic animals and that these related antigens, would provide effective vaccines against parasitism by species of nematode. Species of parasites and hosts they may infect include for example: *Trichinella spiralis* or *Ancylostoma caninum* infections of man, *Strongylus vulgaris* infections of horses, *Trichostrongylus colubriformis* infections of sheep, *Haemonchus contortus* infections of goats, *Ostertagia ostertagi* infections of cattle, *Ascaris suum* or *Trichinella spiralis* infections of pigs, *Toxascaris leonina* or *Uncinaria stenocephala* infections of cats and *Ancylostoma caninum* or *Trichuris vulpis* infections of dogs as well as infections of the circulatory system of man by larvae of Toxocara spp and of the circulatory system of dogs by *Dirofilaria immitis* as well as infections of the circulatory system, urogenital system, respiratory system, skin and subcutaneous tissues of these and other species of animal. It should be noted that this list is by no means complete.

A preparation is described which gives protection against challenge infection by *Haemonchus contortus*. The protective components in the fraction are identified as being soluble in buffers containing low levels of zwitterionic detergents and as not being retained following chromatography on wheat-germ lectin sepharose columns. The protective antigens thus prepared are capable of being further purified by, for example, fractionation on lentil lectin (LL) chromatography or *Helix pomatia* lectin (HpL) chromatography, reverse phase HPLC, size exclusion chromatography or other purification methods known in the art in the presence of solubilizing detergents.

According to a first embodiment of the present invention there is provided a substantially purified antigen derived from a first species of parasitic nematode, which antigen is capable of providing protection to a host from parasitism by a second nematode species, which may be the same as or different from the first nematode species, following vaccination of the host with the antigen, characterized in that the antigen is proteinaceous, has a pI in the range of 3.8–4.4, binds to lentil lectin and *Helix pomatia* lectin and has a molecular weight of approximately 45 kD as determined by reducing SDS-PAGE. Typically the antigen is at least 90% pure. This level of purity is demonstrated with respect to the cleanliness of the preparations used in amino acid sequencing.

The invention encompasses the antigen in both glycosylated and non-glycosylated form.

Typically, the first parasitic nematode species is selected from species of the genera Trichinella, Ancylostoma, Strongylus, Trichostrongylus, Haemonchus, Ostertagia, Ascaris, Toxascaris, Uncinaria, Trichuris, Dirofilaria, Toxocara, Necator, Enterobius, Strongyloides and Wuchereria. Examples of such species include *Trichinella spiralis, Ancylostoma caninum, Strongylus vulgaris, Trichostrongylus colubriformis, Haemonchus contortus, Ostertagia ostertagi, Ascaris suum, Toxascaris leonina, Uncinaria stenocephala, Trichuris vulpis, Dirofilaria immitis,* Toxocara spp, *Necator americanus, Ancylostoma duodenale, Ascaris lumbricoides, Trichuris trichiura, Enterobius vermicularus, Strongyloides stercoralis* and *Wuchereria bancrofti.*

Typically the protection conferred on the host is protection against a parasitic nematode species selected from species of the genera Trichinella, Ancylostoma, Strongylus, Trichostrongylus, Haemonchus, Ostertagia, Ascaris, Toxascaris, Uncinaria, Trichuris, Dirofilaria, Toxocara, Necator, Enterobius, Strongyloides and Wuchereria. Examples of such species include *Trichinella spiralis, Ancylostoma caninum, Strongylus vulgaris, Trichostrongylus colubriformis, Haemonchus contortus, Ostertagia ostertagi, Ascaris suum, Toxascaris leonina, Uncinaria stenocephala, Trichuris vulpis, Dirofilaria immitis,* Toxocara spp, *Necator americanus, Ancylostoma duodenale, Ascaris lumbricoides, Trichuris trichiura, Enterobius vermicularus, Strongyloides Stercoralis* and *Wuchereria bancrofti.*

Preferably the first and second nematode species are selected from the genera Haemonchus, Trichostrongylus and Ostertagia.

More preferably the first and second nematode species are from the genus Haemonchus.

Preferred first and second nematode species are *Haemonchus contortus, Trichostrongylus colubriformus* and *Ostertagia circumcincta.*

More preferably the first and second nematode species are *Haemonchus contortus.*

The present inventors have determined that the antigen of the first embodiment is most likely a proteolytic cleavage product of a higher molecular weight nematode glycoprotein.

The nematode glycoprotein could be prepared from native sources by antibody affinity chromatography using antibodies raised to the expression product of the cloned gene.

The higher molecular weight glycoprotein in glycosylated and unglycosylated form is also encompassed by the present invention and is termed hereinafter the "antigen precursor".

The antigen precursor in substantially purified form is also part of the first embodiment of the present invention.

Typically the antigen precursor comprises the amino acid sequence illustrated in FIG. 8 and in SEQ ID No: 12.

According to a second embodiment of the present invention there is provided a homologue of the antigen or antigen precursor of the first embodiment.

Typically the homologue is at least 70% homologous over 20 amino acids to the amino acid sequence illustrated in FIG. 8 and in SEQ ID No:12.

According to a third embodiment of the present invention there is provided a polynucleotide molecule, excluding polynucleotide molecules as they exist in nature which encodes an antiget or an antigen precursor of the first embodiment, or a homologue of the second embodiment.

Typically the polynucleotide molecule is a DNA molecule.

Preferably the polynucleotide molecule is a cDNA molecule.

Figure 7A:
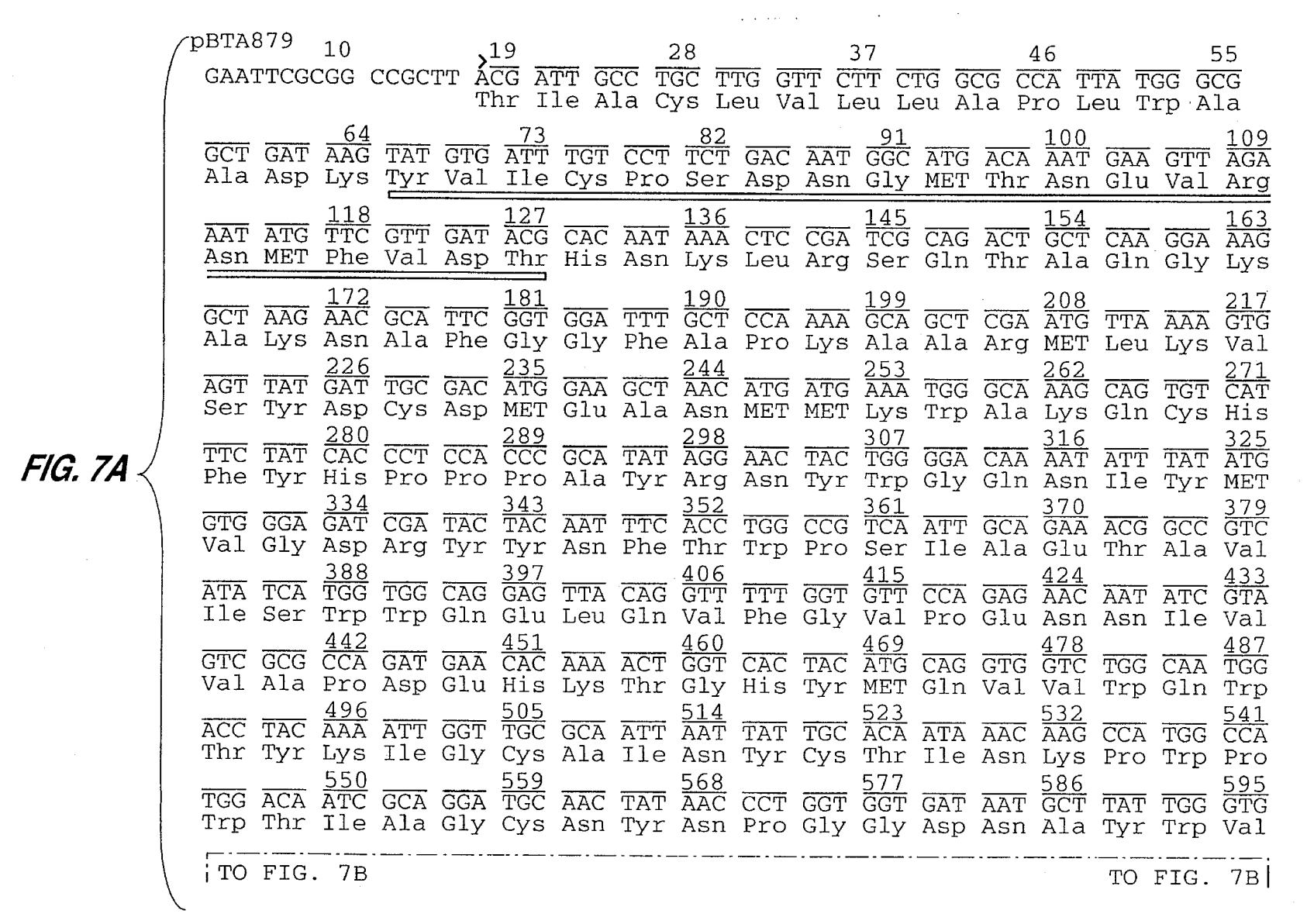

A preferred polynucleotide molecule of the invention is a cDNA molecule having substantially the sequence illustrated in FIG. 7 (SEQ ID No: 9) or 8 (SEQ ID No: 11).

The invention includes within its scope DNA molecules having at least 50% homology over 60 nucleotides with the sequence illustrated in FIG. 8 (SEQ ID No: 11), and encoding a protective molecule capable of conferrring immunity against parasitic nematode infection.

According to a fourth embodiment of the present invention there is provided a recombinant DNA molecule comprising a DNA molecule of the third embodiment and vector DNA.

Typically the vector DNA comprises plasmid, phage or viral DNA.

Preferred vectors include lambda gt11, pUR290, pUR291, pUR282, pUK270, pUC8, pUC9, pZipNeo, an SV40 based vector, lambda gt10, an EMBL vector, pBR327, pBR329, or pBR329 containing a par locus, baculovirus or vaccinia virus.

According to a fifth embodiment of the invention there is provided a transformed host, carrying at least one recombinant DNA molecule according to the fourth embodiment.

Typically the host is selected from bacteria, yeasts, other fungi, insect, plant and mammalian cell lines. Preferred host cells are *E. coli* K12 derivatives.

According to a sixth embodiment of the present invention there is provided an expression product of a transformed host of the fifth embodiment comprising an antigen or antigen precursor of the first embodiment or a homologue of the second embodiment.

The expression product may be a fused expression product.

According to a seventh embodiment of the present invention there is provided a synthetic polypeptide corresponding to all or part of an antigen, precursor, homologue or expression product of the invention which synthetic polypeptide when administered to a host animal is capable of inducing protective immunity against infestation of the host animal by a parasitic nematode.

According to an eighth embodiment of this invention, there is provided a vaccine comprising an effective amount of at least one antigen and/or antigen precursor of the first embodiment and/or a homologue of the second embodiment and/or expression product of the sixth embodiment and/or synthetic polypeptide of the seventh embodiment together with a pharmaceutically and/or veterinarally acceptable carrier, diluent, excipient and/or adjuvant. The vaccines of the invention could alternatively comprise at least one anti-idiotypic antibody capable of protecting a host from infection by a parasitic nematode by mimicking the antigen, antigen precursor, homologue, expression product and/or synthetic polypeptide. A pharmaceutically and/or veterinarally acceptable carrier, diluent, excipient and/or adjuvant may be added to the active component.

As a further alternative, the vaccine may be a whole cell vaccine comprising a transformed host of the fifth embodiment together with a pharmaceutically and/or veterinarally acceptable carrier, diluent, excipient and/or adjuvant. The cells may be live or killed.

The transformed cells include those capable of expressing the expression product for mucosal presentation to a host to be vaccinated, such as, as a cell surface fusion product.

According to a ninth embodiment of this invention there is provided a process for the preparation of an antigen of the first embodiment, which process comprises:

a) homogenizing young adults of a parasitic nematode species to produce an homogenate;

b) obtaining membranous material from the homogenate;

c) extracting the membranous material with a buffer containing low levels of a zwitterionic detergent to obtain a detergent extract;

d) chromatographing the detergent extract on a wheatgerm lectin sepharose column; and e) collecting flow-through from the column.

Preferably, the process also comprises:

f) fractionation by preparative iso-electricfocussing and collection of fractions having a pI in the range 3.8–4.4, or more preferably 4.0–4.3;

g) fractionation by gel filtration chromatography to collect fractions with molecular weights in the range 10–60 kD; and h) fractionation by lentil lectin and/or *Helix pomatia* lectin chromatography and collecting bound material.

According to a tenth embodiment of this invention, there is provided a process for the preparation of a vaccine of the eighth embodiment which process comprises:

admixing an effective amount of at least one antigen and/or antigen precursor of the first embodiment and/or homologue of the second embodiment and/or expression product of the sixth embodiment and/or synthetic polypeptide of the seventh embodiment and/or transformed host of the fifth embodiment and/or antiidiotype antibody with a pharmaceutically and/or veterinarally acceptable carrier, diluent, excipient and/or adjuvant.

According to an eleventh embodiment of this invention, there is provided a method of protecting a host against infection by at least one parasitic nematode species which method comprises administering an effective amount of an antigen and/or antigen precursor of the first embodiment and/or homologue of the second embodiment and/or expression product of the sixth embodiment and/or synthetic polypeptide of the seventh embodiment and/or a vaccine of the eighth embodiment to the host.

According to a twelfth embodiment of this invention, there is provided an antibody raised against an antigen and/or antigen precursor of the first embodiment and/or homologue of the second embodiment and/or expression product of the sixth embodiment and/or synthetic polypeptide of the seventh embodiment and/or a vaccine of the eighth embodiment. The antibody of the invention may be monoclonal or polyclonal. The invention also provides other compounds which behave in a similar manner to the antibodies of the twelfth embodiment, by binding to and altering the structure and/or function of an antigen or antigen precursor of the first embodiment, or homologue of the second embodiment, expression product of the sixth embodiment, or synthetic polypeptide of the seventh embodiment.

According to a thirteenth embodiment of this invention, there is provided an antibody composition comprising an antibody of the twelfth embodiment together with a pharmaceutically and/or veterinarally acceptable carrier, diluent and/or excipient.

According to a fourteenth embodiment of this invention, there is provided a process for the preparation of an antibody of the twelfth embodiment which process comprises vaccinating an immunoresponsive host with an antigen and/or antigen precursor of the first embodiment and/or homologue of the second embodiment and/or expression product of the sixth embodiment and/or synthetic polypeptide of the seventh embodiment and/or a vaccine of the eighth embodiment.

According to a fifteenth embodiment of this invention, there is provided a process for the preparation of an antibody composition of the thirteenth embodiment which process comprises admixing an effective amount of an antibody of the twelfth embodiment with a pharmaceutically and/or veterinarally acceptable carrier, diluent, and/or excipient.

According to a sixteenth embodiment of this invention, there is provided a method of passively vaccinating a host in need of such treatment against a parasitic nematode, which method comprises administering an effective amount of an antibody of the twelfth embodiment and/or an antibody composition of the thirteenth embodiment to the host.

According to a seventeenth embodiment of the present invention there is provided a process for the preparation of a recombinant DNA molecule of the fourth embodiment which process comprises inserting a DNA molecule of the third embodiment into vector DNA.

According to an eighteenth embodiment of the present invention there is provided a process for the preparation of a transformed host of the fifth embodiment which process comprises making a host competent for transformation to provide a competent host and transforming the competent host with a recombinant DNA molecule of the fourth embodiment.

According to a nineteenth embodiment of the present invention there is provided a diagnostic kit comprising a sample of an antigen, antigen precursor, homologue, expression product or synthetic polypeptide of the present invention and/or an antibody of the present invention.

According to a twentieth embodiment of the present invention, there is provided a process for the biosynthesis of an expression product of the sixth embodiment which process comprises providing a transformed host of the fifth embodiment, culturing the host under suitable conditions to obtain expression of the expression product and collecting the expression product from the transformed host.

According to a twenty first embodiment of this invention there is provided an antiidiotype antibody corresponding to a portion of an antiget of the invention and capable of protecting a host immunised with the antiidiotype antibody from infestation by a parasitic nematode species.

It is recognised that variation in amino acid and nucleotide sequences can occur between different allelic forms of a particular protein and the gene(s) encoding the protein. Further once the sequence of a particular gene or protein is known, a skilled addressee, using available techniques, would be able to manipulate those sequences in order to alter them from the specific sequences obtained to provide a gene or protein which still functions in the same way as the gene or protein to which it is related. These molecules are referred to herein as "homologues" and are intended also to be encompassed by the present invention.

In this regard, a "homologue" is a polypeptide that retains the basic functional attribute, namely, the protective activity of an antigen of the invention, and that is homologous to an antigen of the invention. For purposes of this description, "homology" between two sequences connotes a likeness short of identity indicative of a derivation of the first sequence from the second. In particular, a polypeptide is "homologous" to an antigen of the invention if a comparison of amino-acid sequences between the polypeptide and the antigen, reveals an identity of greater than about 70% over 20 amino acids. Such a sequence comparison can be performed via known algorithms, such as the one described by Lipman and Pearson, *Science* 227: 1435 (1985), which are readily implemented by computer.

Homologues can be produced, in accordance with the present invention, by conventional site-directed mutagenesis, which is one avenue for routinely identifying residues of the molecule that can be modified without rendering the resulting polypeptide biologically inactive. Oligonucleotide-directed mutagenesis, comprising [i] synthesis of an oligonucleotide with a sequence that contains the desired nucleotide substitution (mutation), [ii] hybridizing the oligonucleotide to a template comprising a structural sequence coding for an antigen of the invention and [iii] using T4 DNA polymerase to extend the oligonucleotide as a primer, is preferred because of its ready utility in determining the effects of particular changes to the antigen structural sequence. Its relative expense may militate in favour of an alternative, known direct-mutagenesis method.

Also exemplary of antigen homologues within the present invention are molecules that correspond to a portion of the antigen, or that comprise a portion of the antigen without being coincident with the natural molecule, and that display the protective activity of an antigen of the invention.

Other homologues of the present invention are fragments of the antigen that retain protective activity. Likewise within the present invention would be synthetic polypeptides that (i) correspond to a portion of the antigen amino-acid sequence and (ii) retain an activity characteristic of the antigen. Such synthetic polypeptides would preferably be between 6 and 30 amino residues in length.

Whether a synthetic polypeptide meeting criterion (i) also satisfies criterion (ii) can be routinely determined by assaying for protective activity, in an appropriate host.

The amount of antigen, antigen precursor, homologue, expression product and/or synthetic polypeptide to be combined with carrier, diluent, excipient and/or adjuvant to produce a single vaccine dosage form will vary depending upon the infection being vaccinated against, the host to be treated and the particular mode of administration.

It will be understood, also, that the specific dose level for any particular host will depend upon a variety of factors including the activity of the specific antiget, antiget precursor, homologue, expression product and/or synthetic polypeptide employed, the age, body, weight, general health, sex, diet, time of administration, route of administration, rate of excretion, drug combination and the particular infection state being prevented.

The vaccines of the present invention may be administered parenterally or potentially via mucosal routes in dosage unit formulations containing conventional, non-toxic, pharmaceutically and/or veterinarally acceptable carriers, diluents, adjuvants and/or excipients as desired.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

At present alum is the only registered adjuvant for human use however, experimental work is being conducted on other adjuvants for human use and it is anticipated that these other adjuvants would be suitable for use in preparing compositions for human vaccination in accordance with this invention.

Suitable adjuvants for the vaccination of animals include but are not limited to oil emulsions such a Freund's complete or incomplete adjuvant (not suitable for livestock use), Marcol 52: Montanide 888 (Marcol is a Trademark of Esso. Montanide is a Trademark of SEPPIC, Paris), squalane or squalene, Adjuvant 65 (containing peanut oil, mantide monooleate and aluminium monostearate), mineral gels such as aluminium hydroxide, aluminium phosphate, calcium phosphate and alum, surfactants such a hexadecylamine, octadecylamine, lysolecithin, dimethyldioctadecylammonium bromide, N,N-dioctadecyl-N', N'-bis(2-hydroxyethyl) propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate. The antigens, precursors, expression products and/or synthetic polypeptides of the present invention can also be administered following incorporation into liposomes or other micro-carriers, or after conjugation to polysaccharides, proteins or polymers or in combination with Quil-A to form "Iscoms" (Immunostimulating complexes). Other adjuvants suitable for use in the present invention include conjugates comprising the immunogen together with an integral membrane protein of prokaryotic origin, such as TraT. (See PCT/AU87/00107).

Routes of administration, dosages to be administered as well as frequency of injections are all factors which can be optimised using ordinary skill in the art. Typically, the initial vaccination is followed some weeks later by one or more "booster" vaccinations, the net effect of which is the production of vigorous immune response both cellular and humoral.

BRIEF DESCRIPTION OF THE DRAWINGS

FIG. 1 shows gel filtration HPLC results for IEF 5 and 6 on SDS polyacrylamide gel stained with silver. Lanes 1–6 contain GF1–GF6; lane 7 contains Bio-Rad low and high molecular weight standards with sizes given in kilodaltons and lane 8 contains IEF 5 and 6 (pre GF HPLC).

FIG. 2 shows lectin affinity chromatography results for IEF 5 and 6 on an SDS polyacrylamide gel stained with silver. Lane 1 contains molecular weight standards. Lanes 2 and 3 contain material bound and eluted from lentil lectin Sepharose (LLS); lane 4, material that was bound and eluted from *Helix pomatia* lectin Sepharose (HpLS) after initial binding and elution from LLS and lane 5 contains material that did not bind to HpLS after initial binding and elution from LLS.

FIG. 3 shows lectin affinity chromatography results for IEF 5 and 6 as a Western blot overlayed with Concanavalin A-HRP and reactive material visualized by enzymatic reaction. Lane 1 contains IEF 5 and 6; lane 2, material not binding to LLS; lane 3, material bound and eluted from LLS; lane 4, material bound and eluted from HpLS after initial binding and elution from LLS; lane 5, material not bound to HpLS after initial binding and elution from LLS; lane 6, material not bound to LLS or HpLS and lane 7, BRL high molecular weight standards.

FIG. 4 shows lectin affinity chromatography results for IEF 5 and 6 as a Western blot overlayed with *Helix pomatia* lectin - HRP and reactive material visualized by enzymatic reaction. Lane contents are as described for FIG. 3.

FIG. 5 shows reverse-phase HPLC results for IEF 5 and 6 on a PLRP-S column. The gradient used for elution consisted of 30% acetonitrile in water with 0.1% TFA to 60% acetonitrile in water with 0.1% TFA. The flow rate was 1 ml/min and the absorbance monitored at 220 nm. Peak fractions indicated by numbers were collected manually. FIG. 6(*a*) and FIG. 6(*b*) shows reverse-phase HPLC results for IEF 5 and 6, as an SDS polyacrylamide gel (9–22% gradient) stained with silver. Numbers refer to peak fractions shown in FIG. 5. Lane S, Bio-Rad low and high molecular weight standards in the sizes given in kilodaltons.

FIG. 7 shows the cloned DNA sequence (SEQ ID No: 9) of pBTA879 and the derived amino acid sequence (SEQ ID No: 10) of the cloned gene coding a homologue of the protective antigen.

FIG. 8 shows the cloned DNA sequence (SEQ ID No: 11) of pBTA963 and the derived amino acid sequence (SEQ ID No: 12) of the cloned gene coding for the protective antigen.

FIG. 9 shows a Southern blotting of DNA from *H. contortus* hybridised to the cDNA from pBTA879 and pBTA963 showing the presence of homologous genes within the parasite genome. Lane 1. *Haemonchus contortus* DNA, HinfI digest, probed with pBTA963. Lane 2. *Haemonchus contortus* DNA, HinfI digest, probed with pBTA879.

FIG. 10 shows Southern blotting of DNA from *T. colubriformis, Ostertagia circumcincta* and *Ostertagia ostertagi* with a 45 kD antigen probe demonstrating the presence of related genes in other species of nematode. Lane 1. *Haemonchus contortus* DNA, HinfI digest. Lane 2. *Trichostrongylus colubriformis* DNA, HinfI digest. Lane 3. *Ostertagia ostertagi* DNA, HinfI digest. Lane 4. *Ostertagia circumcincta* DNA, HinfI digest. Lane 5. Plasmid pBTA963, HinfI digest - positive control.

Figure 11A:
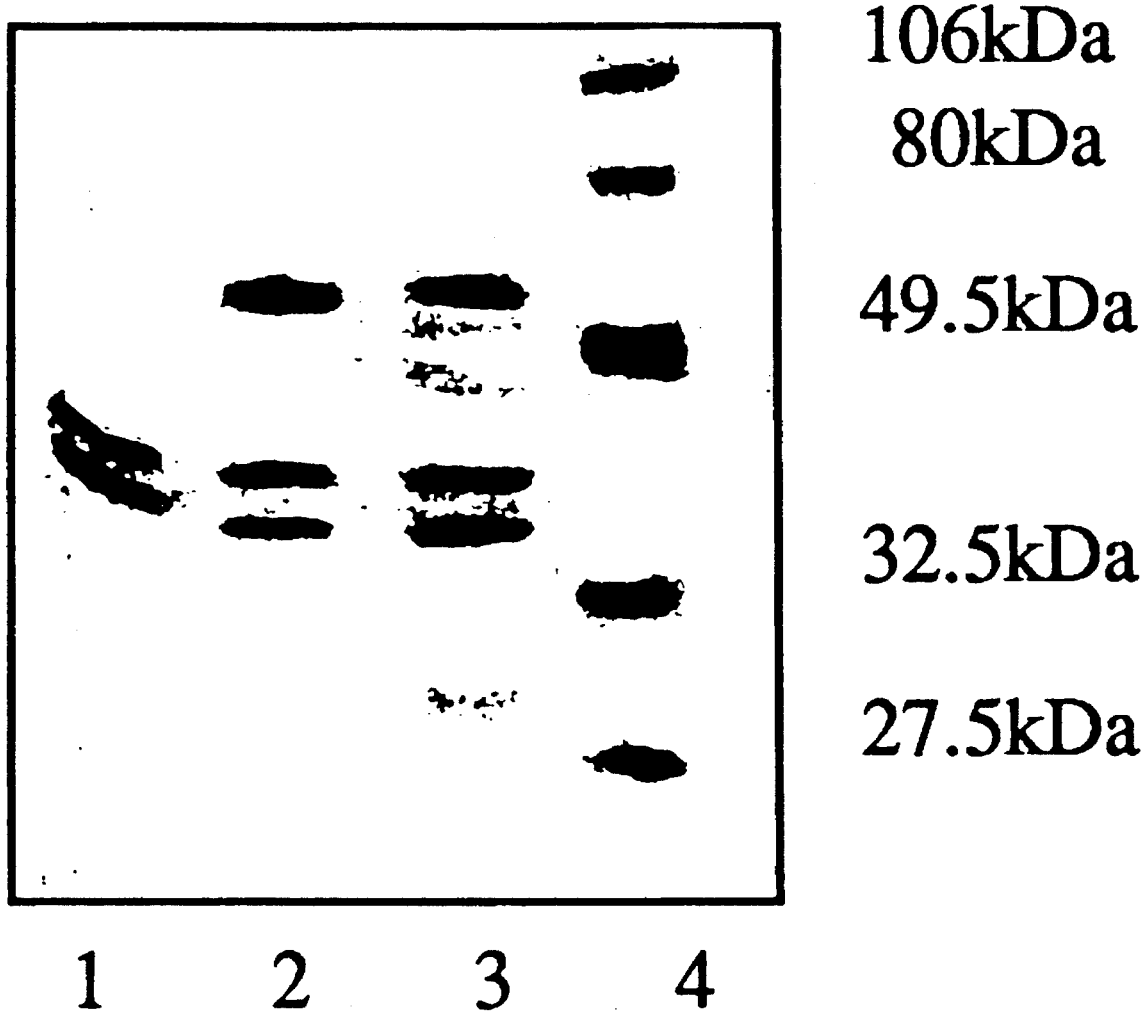

FIG. 11(a) and FIG. 11(b) shows SDS PAGE gels and Western blots of the recombinant 45 kD antigen expressed in *E coli*. FIG. 11(a) Expression of 45 kDa Antigen *E. coli*:Samples were electrophoresed on a 12.5% SDS polyacrylamide gel. The gel was then stained with Coomassie brilliant blue. Lane 1: uninduced control; Lane 2:1 hour post-induction; Lane 3:3 hours post-induction; Lane 4: Biorad prestained SDS PAGE standards. FIG. 11(b) Western Blot of Expressed 45 kDa Antigen: Samples were electrophoresed as in FIG. 11(a), then electrophoretically blotted onto a nitrocellulose filter. The filter was probed with rabbit serum raised against a peptide corresponding to the truncated N-terminus of the 45 kDa protein. The Promega Protoblot alkaline phosphatase system (product no. W3930) was used to develop colour.

Figure 12:
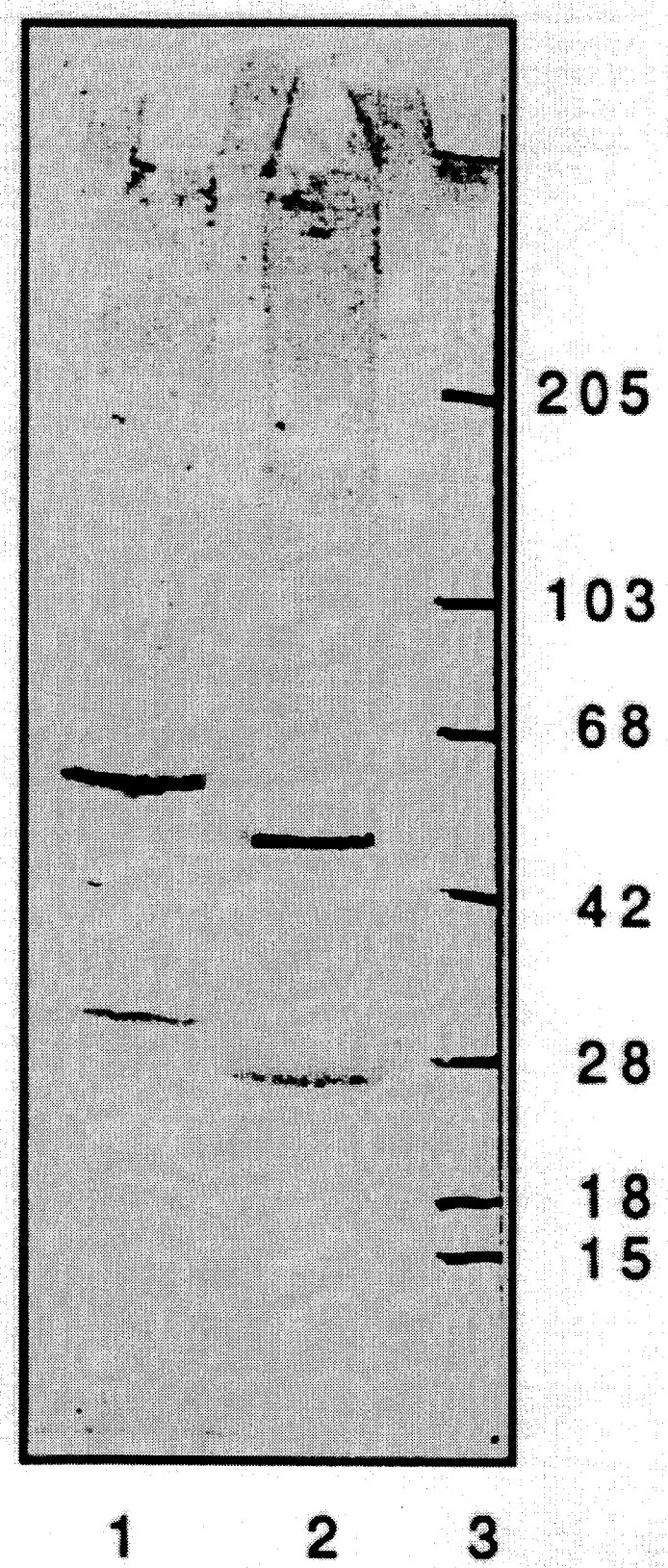

FIG. 12 shows Western blots of extracts from *H. contortus* and the dog heart worm *D. immitis* showing that antigens immunologically related to that of the invention are expressed in other species of parasitic nematode. Lane 1, *D immitis* extract; Lane 2, *H contortus* extract; Lane 3, BRL high molecular weight standards.

BEST METHOD OF CARRYING OUT THE INVENTION

Young adults of *Haemonchus contortus* were homogenised in phosphate-buffered saline (PBS) and the homogenate was centrifuged in order to sediment the membranous material from the nematodes. This pellet was found to protect sheep from challenge infection following two vaccinations. The protective fraction was then extracted with a number of different detergents. Zwittergent 3–14 (Calbiochem) was found to be suitable although other detergents were also found to be effective. Efficiency of extraction was judged by the ability of the detergent used to solubilize protective antigens (as judged by vaccination/challenge experiments), with the highest specific activity (as estimated by the number of micrograms of solubilized material required to give protection) whilst leaving an insoluble residue which failed to give significant protection following the vaccination/challenge protocol employed (42%, see Table 3). It is acknowledged that the Zwittergent 3–14 extraction procedure may not have been completely efficient and some of the protective antigens may be found in the detergent insoluble fraction.

The recombinant DNA molecules and transformed host cells of the invention are prepared using standard techniques of molecular biology.

Expression products of the invention are obtained by culturing transformed host cells of the invention under standard conditions as appropriate to the particular host cell and separating the expression product from the culture by standard techniques. The expression product may be used in impure form or may be purified by standard techniques as appropriate to the expression product being produced.

Where appropriate, whole cells may be used in vaccines.

Synthetic polypeptides of the invention are prepared by standard techniques of peptide synthesis based on the known sequences of antigens, antigen precursors, homologues and expression products of the invention.

The homologues, expression products and synthetic polypeptides can be tested for protective activity as described in the following examples. Recombinant DNA technology can be used to provide a large amount of the protective antigen or homologues described herein. The DNA segment coding for the protective antigen or the precursor for the protective antigen or homologue can be inserted into any of a number of recombinant plasmid systems to enable the molecule to be synthesised in large amounts. The recombinant systems include *E. coli*, yeast, and baculovirus systems and viruses such as vaccinia. The recombinant organisms can be grown in large volumes in fermenters and the recombinant antigens purified by standard methods - solubilisation in solutions containing urea and reducing agents such as DTT or mercaptoethanol, refolding in the presence of reagents such as reduced and oxidised glutathione, purification by ion exchange, filtration and/or gel permeation chromatography, terminally sterilised by filtration and adjuvanted in any of a number of adjuvants including oils.

The vaccine is prepared by mixing, preferably homogeneously mixing, an antigen, antigen precursor, homologue, expression product and/or synthetic polypeptide and/or transformed host and/or antiidiotype antibody of the invention with a pharmaceutically and/or veterinarally acceptable carrier, diluent, excipient and/or adjuvant using standard methods of pharmaceutical and/or veterinary preparation.

The amount of antigen, antigen precursor, homologue, expression product, synthetic polypeptide and/or transformed host and/or antiidiotype antibody required to produce a single dosage form will vary depending upon the infection being vaccinated against, host to be treated and the particular mode of administration. The specific dose level for any particular host will depend upon a variety of factors including the age, body weight, general health, sex and diet of the host, time of administration, route of administration, rate of excretion and drug combination.

The vaccine may be administered parenterally in unit dosage formulations containing conventional, non-toxic, pharmaceutically and/or veterinarally acceptable carriers, diluents, excipients and/or adjuvants as desired.

Antiidiotypes are raised by vaccinating a suitable host with an antigen, precursor, expression product, homologue and/or synthetic polypeptide of the invention and using the resulting antibodies to raise antibodies against the antigen binding region of the antibodies raised in the first vaccination.

Antibodies are raised using standard vaccination regimes in appropriate hosts. The host is vaccinated with an antigen, antiget precursor, homologue, expression product, synthetic polypeptide and/or vaccine of the invention. An immune response is generated as result of vaccination. The immune response may be monitored, for example, by measurement of the levels of antibodies produced.

The antibody composition is prepared by mixing, preferably homogeneously mixing, antibody with a pharmaceutically and/or veterinarally acceptable carrier, diluent, and/or excipient using standard methods of pharmaceutical and/or veterinary preparation.

The amount of antibody required to produce a single dosage form will vary depending upon the infection being vaccinated against, host to be treated and the particular mode of administration. The specific dose level for any particular host will depend upon a variety of factors including the age, body weight, general health, sex, and diet of the host, time of administration, route of administration, rate of excretion, drug combination and the severity of the infection undergoing treatment.

The antibody composition may be administered parenterally, in unit dosage formulations containing conventional, non-toxic, pharmaceutically and/or veterinarally acceptable carriers, diluents, and/or excipients as desired, to passively protect hosts against nematode infestation.

Diagnostic kits are prepared by formulating expression product, antibodies, antiget, antigen precursor, homologue or synthetic polypeptide at appropriate concentration to the substance(s) to be detected with a pharmaceutically and/or veterinarally acceptable carrier, diluent and/or excipient. A positive control standard of a known concentration of the substance to be detected is prepared similarly. The negative standard comprises carrier, diluent and/or excipient alone.

The invention is further described with reference to the following examples, which are not limiting on the scope of the present invention.

EXAMPLE 1

Young H. contortus nematodes were recovered from infected sheep. The nematodes were washed three times in PBS and homogenised in PBS. The homogenate was centrifuged at 500×g for 10 min to remove large and unbroken worm material. The supernatant was then centrifuged at 120,000×g av for 2 hours at 4° C. The pelleted material was suspended in PBS and then used to vaccinate sheep subcutaneously in the absence of adjuvant on two occasions four weeks apart, each vaccination containing approximately 50 mg worm wet weight equivalent per kg body weight of the sheep. Three weeks after the second vaccination the sheep and five non-vaccinated infection controls were challenged with 10,000 infective larvae of Haemonchus contortus. On days 23, 27, 28, 33, 36 and 40 post infection, faecal egg counts were performed on all sheep. The results (eggs/g faeces) are presented in Table 1.

TABLE 1

| | Faecal Egg Counts Eggs/g Faeces | | | | | |
|---|---|---|---|---|---|---|
| | Day | | | | | |
| Animal | 23 | 27 | 29 | 33 | 36 | 40 |
| Controls | | | | | | |
| 1 | 1,433 | 4,300 | 2,800 | 6,467 | 4,267 | 5,900 |
| 2 | 700 | 3,633 | 3,400 | 7,367 | 7,267 | 8,600 |
| 3 | 600 | 4,467 | 4,767 | 4,033 | 4,367 | 7,800 |
| 4 | 667 | 10,200 | 11,400 | 18,333 | 16,533 | 6,100 |
| 5 | 3,200 | 5,333 | 5,133 | 7,367 | 4,433 | 6,700 |
| Vaccinates | | | | | | |
| 6 | 33 | 300 | 267 | 567 | 2,133 | 1,350 |
| 7 | 6,167 | 14,434 | 8,000 | 22,434 | 11,133 | 16,550 |
| 8 | 33 | 33 | 0 | 33 | 1,333 | 850 |
| 9 | 0 | 0 | 67 | 67 | 767 | 1,350 |
| 10 | 0 | 0 | 0 | 0 | 133 | 0 |

It is clear that four of the five vaccinated animals were well protected from infection ($p < 0.02$ for the vaccinated group vs control group).

EXAMPLE 2

A series of experiments was conducted in which female guinea pigs were vaccinated with homogenates of adult H. contortus and with 120,000 ×g pellets and supernatants derived from those homogenates (prepared essentially as described in Example 1). The guinea pigs received two vaccinations intraperitoneally in the absence of adjuvant three to four weeks apart and were challenged three to four weeks after the second vaccination with 1,000 infective larvae of H. contortus. Five to six days following infection, the animals were sacrificed and worm counts performed.

Table 2 summarises the results of these experiments showing the worms recovered from the vaccinates as a percentage of those recovered from control non-vaccinated animals receiving the same challenge infection.

TABLE 2

| Fraction | % Protection | Experiment No. |
|---|---|---|
| Homogenate | 61 | 163 |
| Homogenate (3 groups) | 45, 55, 45 | 165 |
| 120,000 × g pellet | 59 | 196 |
| 120,000 × g pellet | 34* | 171 |
| 120,000 × g supernatant | 29 | 196 |
| 120,000 × g supernatant | 15* | 149 |

*These animals only received one vaccination.
It is clear from these results that fractions derived from homogenates of adult H. contortus are capable of giving significant protection to guinea pigs, particularly the particulate material found in the 120,000 × g pellet.

EXAMPLE 3

Young adult H. contortus were homogenised in Tris buffered saline and a 120,000× g pellet prepared as described in Example 2. The pellet was resuspended in Tris buffered saline (TBS) containing 1% (WV) Zwittergent SB-14 (Sigma) by sonication and shaking at 4° C. for 1 hour. The extract was centrifuged at 50,000× gav for 30 minutes to pellet the detergent insoluble material. The supernatant fraction was passed over an affinity column of wheat germ lectin-sepharose 6MB (Sigma) on two occasions to separate glycoproteins containing terminal N-acetyl-glucosamine residues. The five fractions derived from this procedure were used to vaccinate guinea pigs as described in Example 2. The results (Table 3) clearly demonstrate that a significant portion of the protective material was solubilized in the detergent, but the majority of the protective antigen(s) failed to bind to wheat germ lectin.

TABLE 3

| Fraction | μg/animal | % Protection |
|---|---|---|
| SB-14 insoluble material | 800 μg | 42% |
| SB-14 soluble material | 700 μg | 71% |
| SB-14 soluble WGA$^+$ | 10 μg | 22% |
| SB-14 soluble WGA$^-$ | 700 μg | 77% |

WGA$^+$ is wheat germ agglutinin binding material
WGA$^-$ is wheat germ agglutinin non-binding material
SB-14 is Zwittergent SB-14 (Calbiochem).

Material contained in a particulate preparation derived from a homogenate of H. contortus, when used to vaccinate guinea pigs or sheep, is capable of promoting an immune response in the vaccinated animals which gives rise to reduced parasitism in those animals when they are infected with the parasite. The protective antigens are largely soluble in detergents such as Zwittergent SB-14 and do not bind to wheat germ agglutinin under the conditions employed in the above examples.

EXAMPLE 4

A Zwittergent SB-14 extract was prepared from 10–15 g wet weight of young adult H. contortus as described in Example 3, and used to vaccinate sheep in two experiments.

The animals received two vaccinations three weeks apart, the first in Freund's complete adjuvant and the second in Freund's incomplete adjuvant. Three weeks after the second vaccination, the sheep were challenged per os with 10,000 larvae of *H. contortus*. Faecal egg counts were performed twice per week starting 21 days post infection for the next 4 weeks at which time the animals were slaughtered for worm counts (Table 4a and 4b). It is clear that the Zwittergent SB-14 extract contained antigens which were capable of giving significant protection in sheep against infection as measured by either faecal egg counts or worm counts, in spite of the fact that the amount of protein used to vaccinate each animal in the experiment was very small (10±2.5 mg) and the extract contained a large number of components as judged by SDS polyacrylamide gel electrophoresis.

TABLE 4a

|  | Challenge Controls | SB-14 in Adjuvant Controls | SB-14 Extract of H.c. L5 in Adjuvant |
|---|---|---|---|
| Group average faecal egg counts | 21080 | 18623 | 7844 |
| % Protection cf adjuvant controls |  |  | 62.8 |
| Worm counts of sheet at slaughter | 3874 | 3774 | 1422 |
| % Protection of adjuvant controls |  |  | 63.3 |

TABLE 4b

|  | Challenge Controls | SB-14 in Adjuvant Controls | SB-14 Extract of H.c. L5 in Adjuvant |
|---|---|---|---|
| Group average faecal egg counts | 36643 | 75600 | 9114 |
| % Protection cf Adjuvant Controls |  |  | 88 |
| Worm Counts of sheep at slaughter | 1096 | 2117 | 533 |
| % Protection cf adjuvant controls |  |  | 75 |

EXAMPLE 5

For the same experiment as in Example 3, five times more material was prepared than that used in that Example. The remaining Zwittergent SB-14 extract (approximately 63 mg of protein) was fractionated by preparative isoelectric focussing in a 4% Ultrodex resin (LKB) containing Pharmalyte 3–10 ampholines and 0.5% CHAPS detergent (Calbiochem). Following electrophoresis for 10000 Vh, the bed was scraped into 30 fractions and the material in each fraction was eluted in 0.1% CHAPS. The pH of each fraction was determined and each fraction was then concentrated to 1 ml on a YM10 membrane. An aliquot of each fraction was analysed by SDS polyacrylamide gel electrophoresis and stained with Coomassie brilliant blue. Aliquots (approximately ⅛) of each fraction were pooled based on the components visualised on the SDS gel giving a total of 5 fractions which were used to vaccinate guinea pigs as described in Example 2. Worm counts (Table 5) show that the majority of the protective antigen(s) is contained in Fractions 1–10 of the IEF gel which covers the pI range of 3.3–4.6. Other fractions also contained material which resulted in a decrease in worm burdens and these are also of interest in this application.

TABLE 5A

Experiment #229

| Fraction | pI | Worm Counts | % Protection |
|---|---|---|---|
| Controls |  | 467 ± 190 | — |
| SB-14 Extract |  | 226 ± 62 | 52% |
| IEF 1–10 | 3.3–4.6 | 233 ± 155 | 50% |
| IEF 11–14 | 4.7–5.3 | 341 ± 112 | 37% |
| IEF 15–18 | 5.4–6.2 | 323 ± 107 | 31% |
| IEF 19–22 | 6.6–7.5 | 528 ± 33 | 0 |
| IEF 23–30 | 7.7–9.3 | 347 ± 247 | 26% |

TABLE 5B

Experiment #250

| Fraction | pI | Worm Counts | % Protection |
|---|---|---|---|
| Controls |  | 664 ± 152 | — |
| SB-14 Extract |  | 254 ± 111 | 62% |
| IEF 1–10 | 3.3–4.6 | 238 ± 67 | 64% |
| IEF 11–14 | 4.7–5.3 | 274 ± 287 | 59% |
| IEF 15–18 | 5.4–6.2 | 455 ± 251 | 31% |
| IEF 19–22 | 6.6–7.5 | 474 ± 427 | 28% |
| IEF 23–30 | 7.7–9.3 | 356 ± 100 | 46% |

For the second experiment in Example 4, the results of which are presented in Table 4b, groups of sheep were vaccinated with similar broad range IEF fractions as in the above example. The results are presented in Table 5c.

TABLE 5c

| Fraction | Group Average Faecal egg counts | Group Average Worm counts | % Protection cf adjuvant controls Egg Counts | % Protection cf adjuvant controls Worms |
|---|---|---|---|---|
| Adjuvant controls SB-14 | 75600 | 2117 | — | — |
| Extract | 9114 | 533 | 88 | 75 |
| IEF 1–10 | 26314 | 1440 | 65 | 32 |
| IEF 11–14 | 27814 | 395 | 63 | 81 |
| IEF 15–18 | 24271 | 503 | 68 | 76 |
| IEF 19–22 | 16917 | 581 | 78 | 73 |
| IEF 23–30 | 27329 | 956 | 64 | 55 |

This data corroborates that obtained in the guinea pig vaccination and challenge experiments in that it clearly demonstrates that there are antigens in the IEF fractions 1–10 which are capable of providing significant degrees of protection to sheep against *H. contortus* challenge infections. It is also clear from these data that there are additional protective components in the other IEF fractions examined in this experiment and these are of interest in this application as well as those contained in IEF fractions 1–10.

EXAMPLE 6

Half of the first 10 IEF fractions used in Example 5 were pooled in pairs and used to vaccinate guinea pigs. The worm counts (Table 6) show the majority of the protective material was contained in fractions 5 and 6 from the original IEF gel which contains material with a pI of 3.8–4.4.

TABLE 6

| Fraction | pI | Worm Counts | % Protection |
|---|---|---|---|
| Controls | | 589 ± 194 | — |
| IEF 1–10 | 3.3–4.6 | 183 ± 85 | 69% |
| IEF 1 & 2 | 3.3–3.5 | 509 ± 122 | 13% |
| IEF 3 & 4 | 3.7–3.8 | 373 ± 143 | 37% |
| IEF 5 & 6 | 4.0–4.3 | 225 ± 103 | 62% |
| IEF 7 & 8 | 4.4–4.5 | 321 ± 115 | 45% |
| IEF 9 & 10 | 4.5–4.6 | 335 ± 223 | 43% |

When aliquots of the IEF fractions were electrophoresed on SDS polyacrylamide gels and stained with silver, a number of components could be visualized which seemed to be enriched in the pI 3.8–4.4 fractions. Some of these were not sharp bands and are presumably 15 glycoproteins. The apparent molecular weight of these compounds compared with BRL high molecular weight protein standards were 100–120 kD, 40–55 kD, a cluster of perhaps 5 components in the 14–20 kD range and material not resolved by the gel at molecular weight less than 15 kD. In addition there was a sharp doublet of proteins with apparent molecular weights of 32–36 kD which were more abundant however in neighbouring less protective fractions and are therefore considered unlikely to be the antigens responsible for the protective immune responses. The IEF fractions were also used in "Western blots" using serum from sheep vaccinated in Example 4 as indicator serum. All of the components in the pI 3.8–4.4 range which were observed in the silver stained gels reacted with the sheep serum and are therefore capable of eliciting an immune response in sheep under the vaccination regime carried out in that experiment. These results indicate that potentially protective antigens can be isolated from young adult *H. contortus* which are particulate, solubilized at least in part with 1% Zwittergent SB-14, have a pI in the range of 3.8–4.4 and may have apparent molecular weights of 100–120 kD, 40–55 kD, 14–20 kD or less than 15 kD as estimated by SDS gel electrophoresis and compared with BRL high molecular weight markers.

EXAMPLE 7

IEF fractions 5 and 6 were dialysed against 50 mM sodium phosphate buffer pH 6.6 containing 0.6% CHAPS and concentrated six-fold on a YM-10 membrane. 0.2 ml aliquots were fractionated by HPLC gel filtration using a Bio-Sil TSK-400 column (30×0.75 cm.) (Bio-Rad) in the same buffer at a flow rate of 0.2 ml/min and eluent absorbance monitored at 280 nm. Fractions were collected and pooled on the basis of eluent absorbance profile. The fractions present in the last eluting peak were pooled and re-chromatographed on a TSK-SW 3000 G gel filtration column (Toyo Soda) using the conditions described above. A total of six pools were used to vaccinate guinea pigs as described in Example 2; each pool contained the equivalent of 4 ml IEF 5 and 6. Worm counts (Table 7) show that the majority of the protective antigen(s) is contained in GF 5 and GF 6 which include antigens in an approximate molecular weight range from < 10 kD to 60 kD.

TABLE 7

| Fraction | M.W. Range (kD) | Worm Counts | % Protection |
|---|---|---|---|
| Controls | — | 436 ± 123 | — |
| IEF 5 and 6 | <10–>250 | 224 ± 125 | 49 |
| GF 1 | >250 | 369 ± 104 | 15 |
| GF 2 | 100–>250 | 344 ± 158 | 21 |
| GF 3 | 55–>250 | 341 ± 168 | 22 |
| GF 4 | 55 | 387 ± 105 | 11 |
| GF 5 | <10–60 | 233 ± 141 | 47 |
| GF 6 | <10–44 | 237 ± 170 | 46 |

When aliquots of the gel filtration pools were electrophoresed on SDS polyacrylamide gels and stained with silver, a number of components could be visualized which seemed to be enriched in GF 5 and GF 6 (FIG. 1). The apparent molecular weight of these compared with Bio-Rad low molecular weight standards were 45 kD, perhaps four indistinct components in the 25–30 kD range and perhaps five proteins in the 14–20 kD range. There are also other components that are unresolved on this gel and co-migrate at the buffer front.

Components resident in GF 5 and GF 6 could be more highly resolved by several means. The methods described in Examples 8 and 9 are by way of illustration only.

EXAMPLE 8

Figure 2:
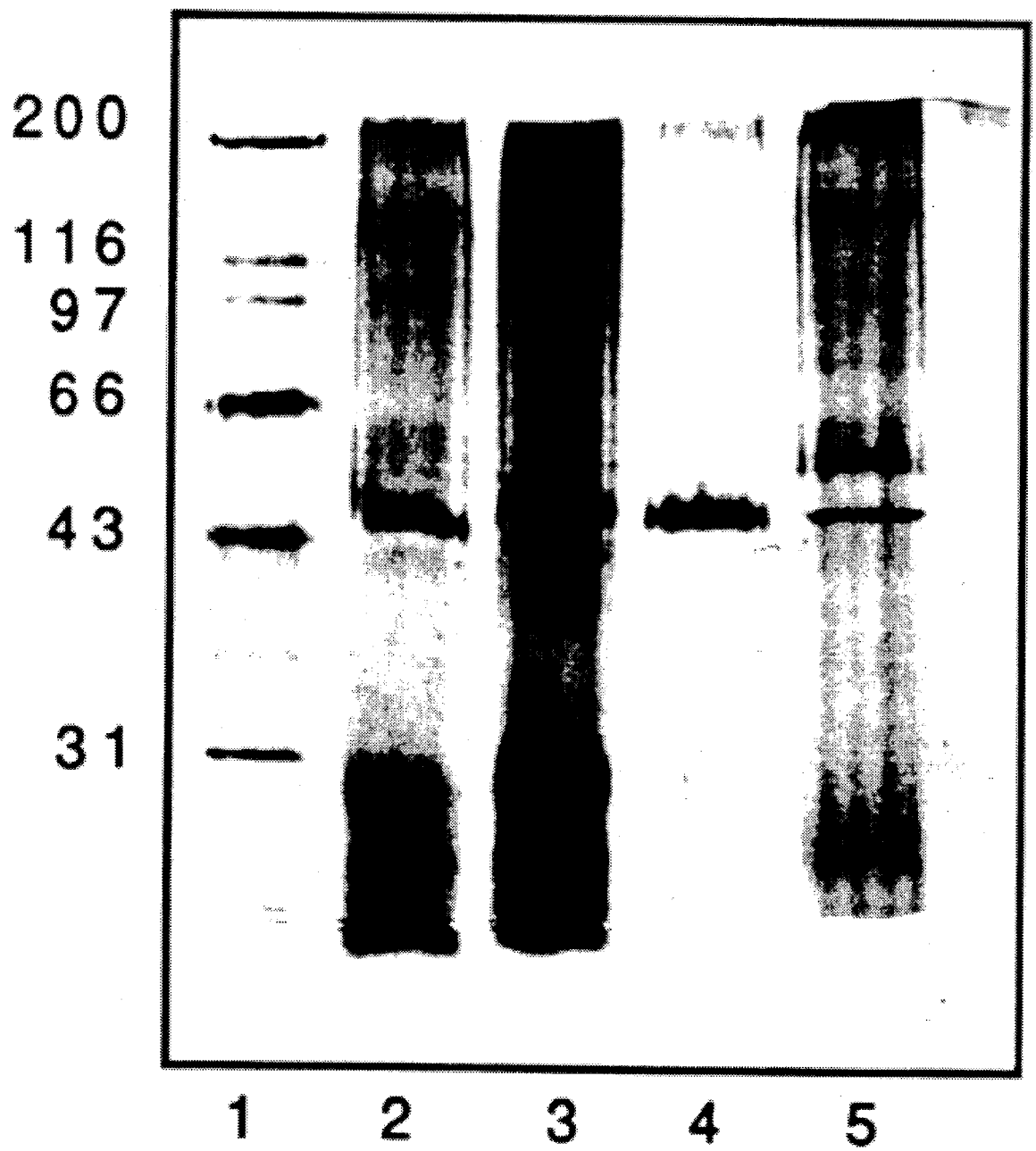
Figure 3:
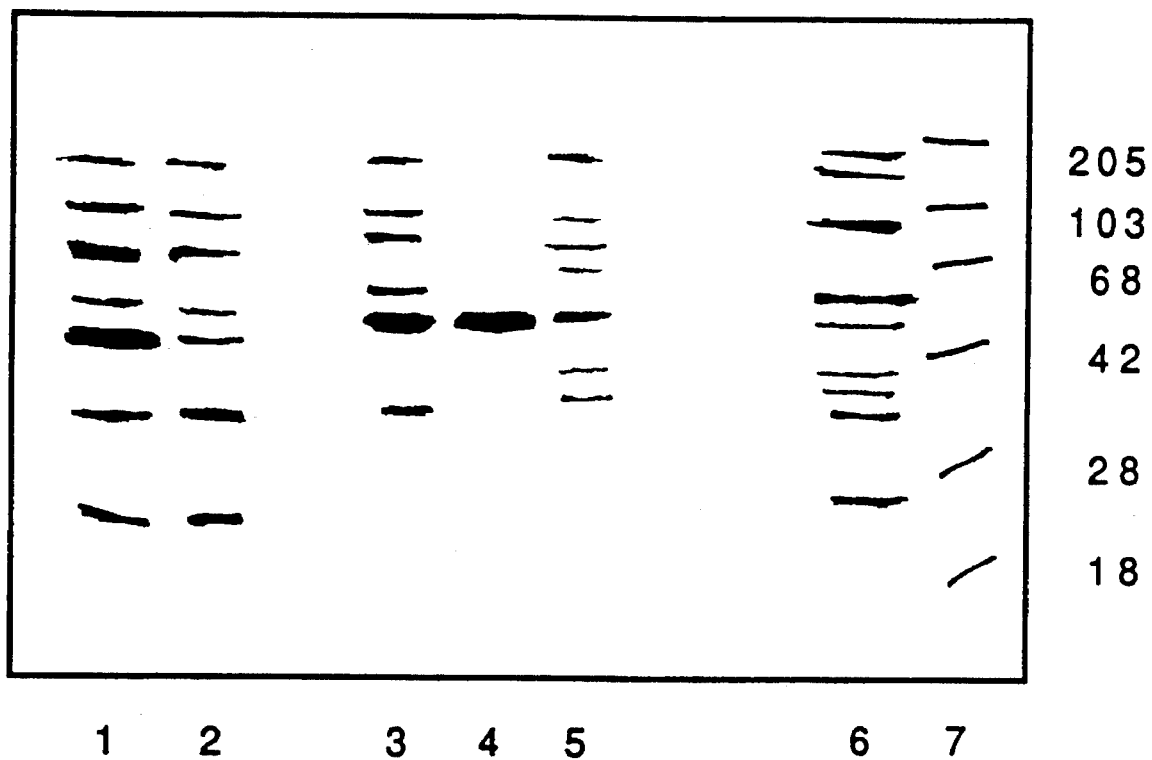
Figure 4:
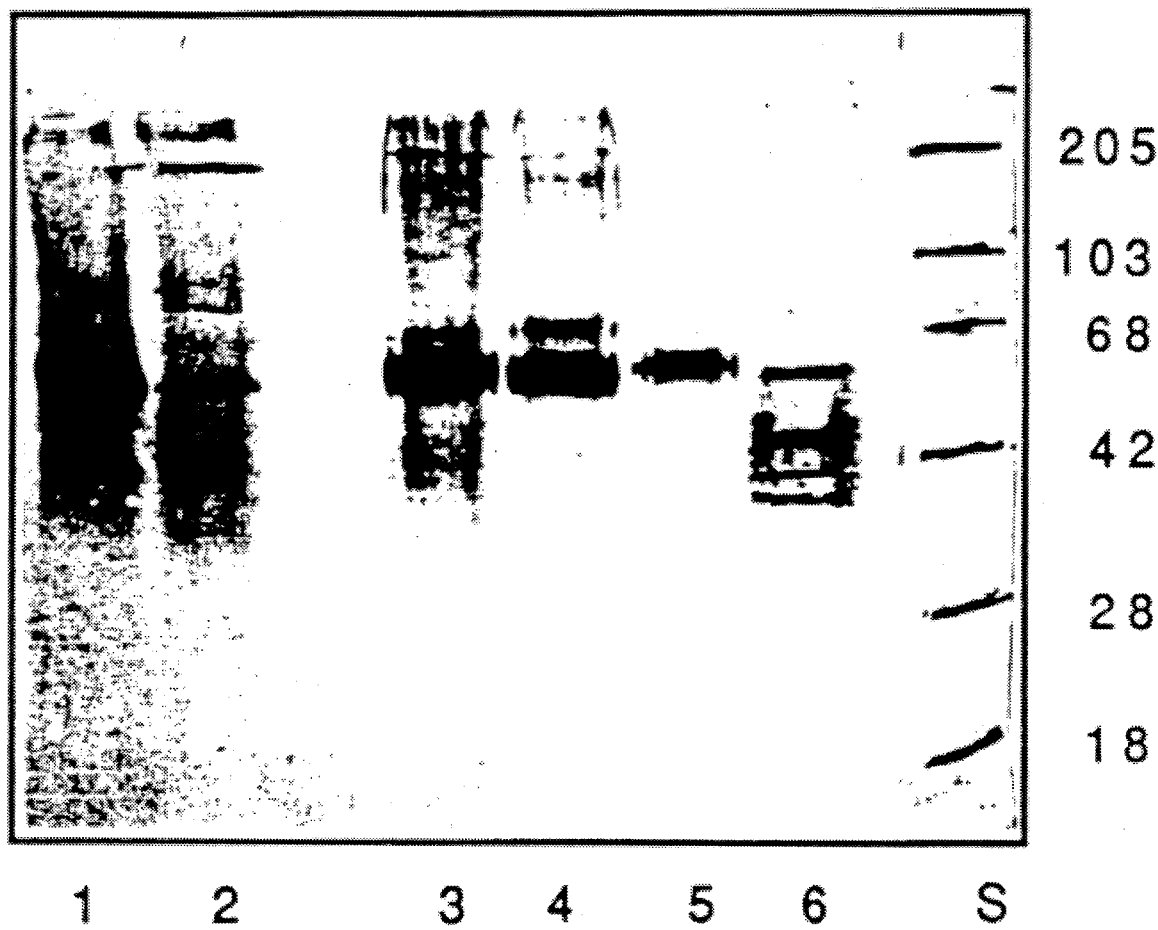

6 ml IEF 5 and 6 was diluted with an equal volume of 100 mM Tris/250 mM sodium chloride pH 7 and stirred with 0.5 ml of lentil lectin-Sepharose 4B (Pharmacia) for 16 h at 4° C. The Sepharose conjugate was removed by centrifugation for 1 min at 3,000×g, washed four times with 50 mM Tris-saline buffer pH 7 containing 0.1% Zwittergent SB-14 (TSZ buffer) then eluted with the same buffer to which had been added 0.3M methyl-α-D-mannopyranoside. Half of the lentil lectin bound fraction was stirred with 0.5 ml *Helix pomatia* lectin-Sepharose 6MB (Pharmacia) for 16 h at 4° C., the conjugate washed four times in TSZ buffer and then eluted in TSZ buffer containing 0.2M N-acetyl-D-galactosamine. Aliquots of all fractions were run in triplicate on SDS polyacrylamide gels before 1) staining with silver (FIG. 2) or Western transfer and 2) staining with Concanavalin A horse radish peroxidase (HRP) conjugate (Sigma) (FIG. 3) or 3) staining with *Helix pomatia* lectin-HRP (Sigma) (FIG. 4). The silver stained gel shows a predominant protein of 45 kD which binds to both lentil and *Helix pomatia* lectins; the latter does not bind minor contaminant proteins. These observations are confirmed by the two lectin blots (Concanavalin A has the same sugar specificity as lentil lectin).

Guinea pigs were vaccinated as described in Example 2 with samples of the fractions of IEF 5 and 6 following fractionation by lectin affinity chromatography as outlined above. Worm counts at slaughter (Table 8) showed that protection was afforded by the lectin-bound fraction. Other fractions also afforded some protection in this experiment. This could be due to incomplete removal of the 45 kD component from the IEF fraction 5 & 6 by the lectins as the antigen may exist in various forms with different degrees of glycosylation (although little material of this molecular weight can be seen on the SDS gel profiles of the *Helix pomatia* lectin unbound fraction). The protection obtained with the other fractions could also be due to the presence in those fractions of other protective antigens. These other antigens are of interest, here.

TABLE 8

| Fraction | Worm Counts | % Protection |
|---|---|---|
| Controls | 462 ± 320 | 0 |
| IEF 5 and 6 | 273 ± 238 | 41 |
| Lentil lectin bound (LL⁺) | 315 ± 127 | 32 |
| Lentil lectin unbound (LL⁻) | 207 ± 288 | 55 |
| LL⁺, *Helix pomatia* lectin bound | 221 ± 150 | 52 |
| LL⁺, *Helix pomatia* lectin unbound | 218 ± 114 | 53 |

EXAMPLE 9

Figure 5:
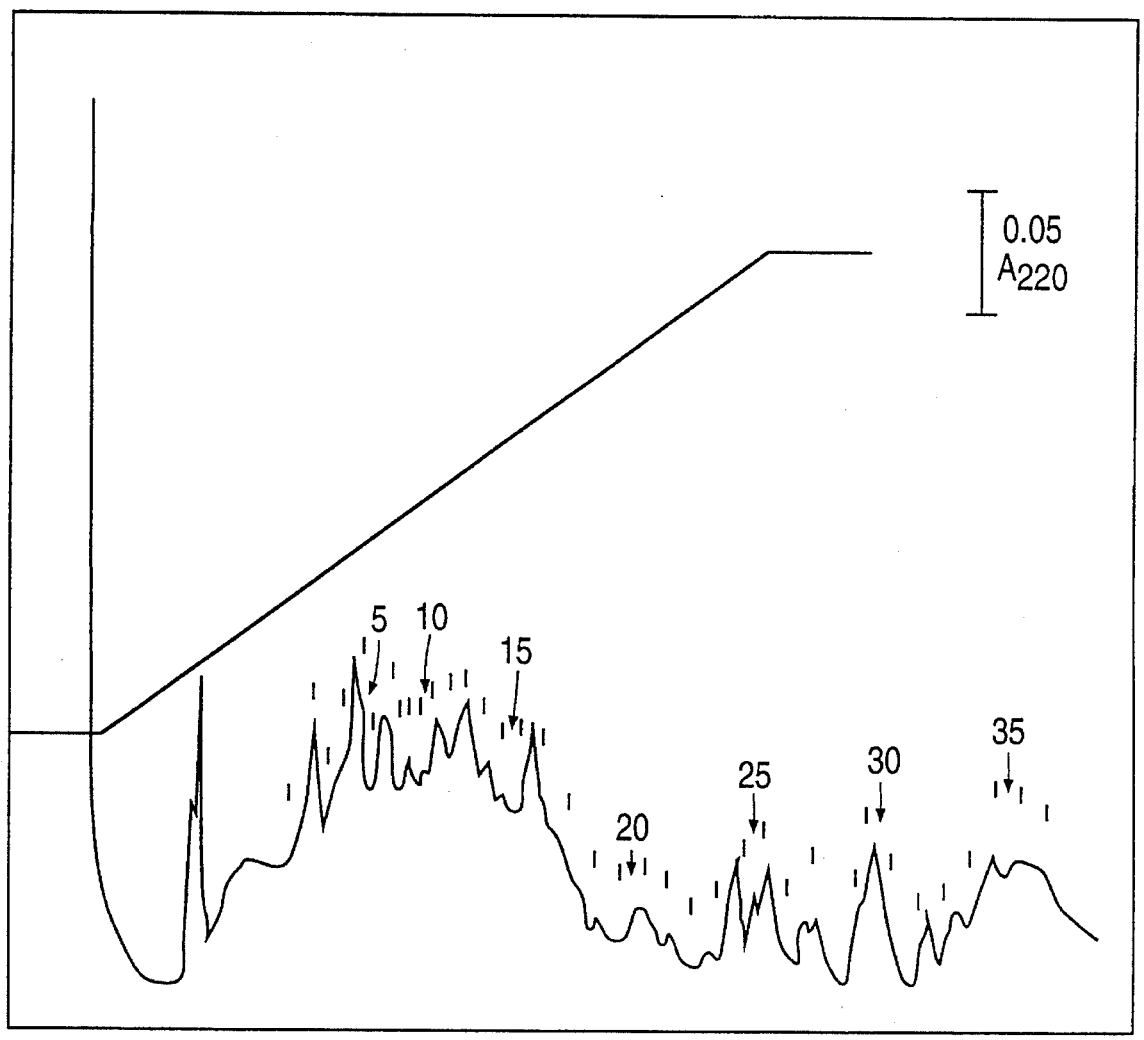
Figure 6A:
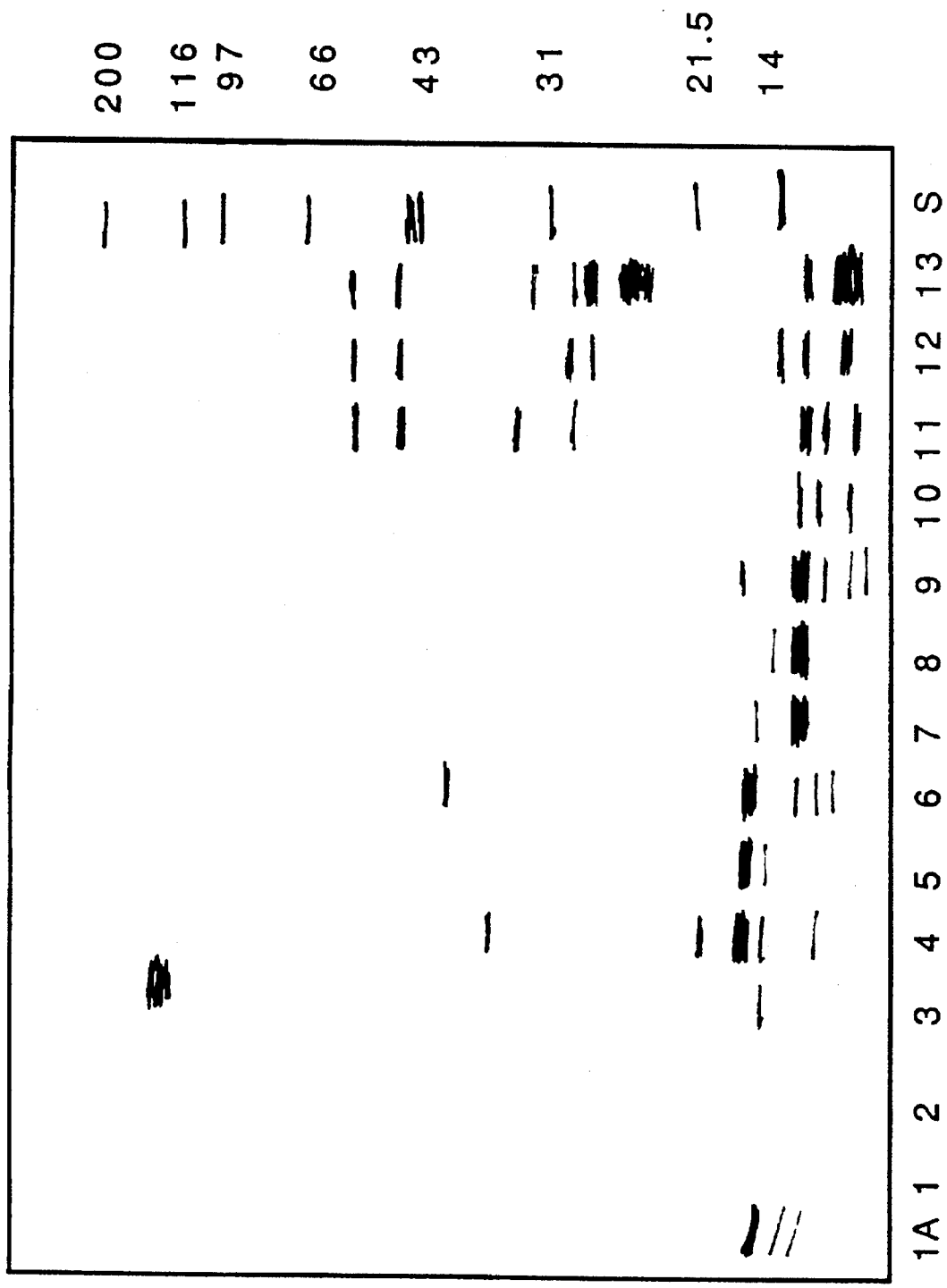
Figure 6B:
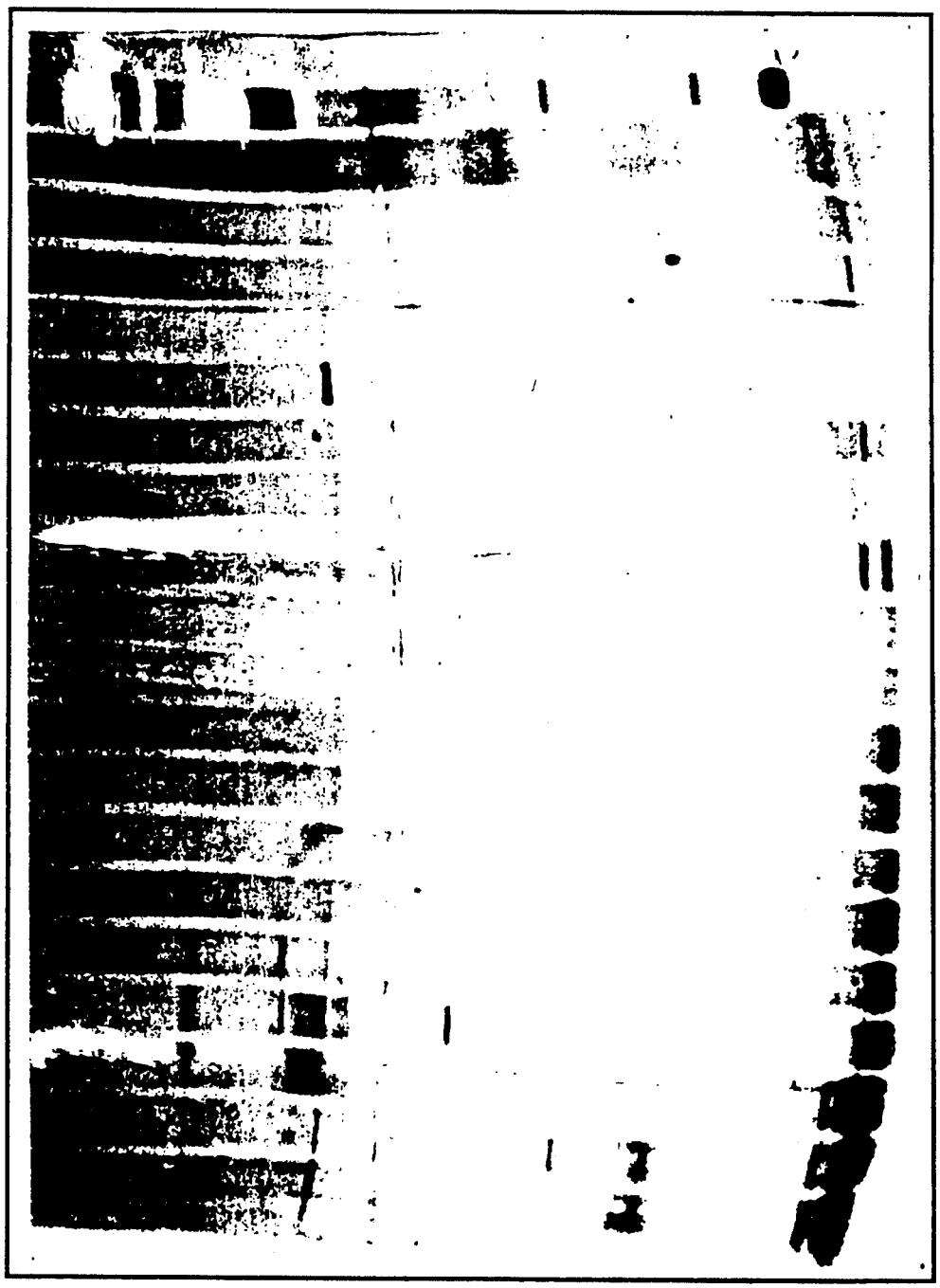

IEF 5 and 6 was dialysed against 20 mM Tris/1 mM EDTA pH 7.5 and then concentrated ten-fold using a YM-10 membrane. 0.3 ml aliquots were acidified by the addition of trifluoroacetic acid (TFA) to a concentration of 0.1% and then centrifuged to remove any precipitate. The supernatant was injected onto a PLRP-S reverse phase HPLC column (Polymer Laboratories) equilibrated in 30% acetonitrile/ 0.1% TFA and developed with a linear gradient over 30 min until 60% acetonitrile/0.1% TFA was achieved. Eluent absorbance was monitored at 220 nm (FIG. 5) and fractions collected across the gradient. Selected fractions were run on SDS polyacrylamide gels and stained with silver (FIG. 6) to show that most of the proteins present in the starting material were recovered and were highly resolved.

These data demonstrate that the antigens in the protective fraction could be well resolved by reverse phase HPLC but further studies demonstrated that the material was no longer protective to guinea pigs following vaccination. Presumably treatment of the antigen fraction with the solvents used on the reverse phase HPLC denatured the antigens so that they no longer resembled the structure of the native antigens.

EXAMPLE 10

In order to remove the detergent, concentrate the sample, remove salts and exchange the antigen into a buffer suitable for amino acid sequence analysis, the lentil lectin bound, *Helix pomatia* bound antigen of approximately 45 kD was fractionated by reverse phase HPLC on a Polypore phenyl RP (30×2.1 mm) column and resolved over 20 minutes with a gradient of from 0.1% TFA/10% acetonitrile to 0.07% TFA/70% acetonitrile (flow rate 200 u l/min). The 45 kD antigen was eluted toward the centre of the gradient as a major peak with a small shoulder. The two fractions were collected separately but appear to be composed of the same polypeptide based on the N-terminal amino acid sequence data obtained.

```
A F   X P G   S N N G M (T) D E I R Q I F (V) (D) (K)
   (Y)(H)    (D)(N)              (S) (G)(G)
                (P)                  (P)(P)
                                        (D)
```

The N-terminal amino acid sequence of the fractions was determined by gas phase sequencing on an Applied Biosystems model 470 1 A amino acid sequencer. The following sequence was obtained (Seq ID No:1)

(SEQ ID NO: 2)
(K) X X (P) (D) X E V E A N (T) A A Y A (N) E (E)
      (Y)              (S)

(SEQ ID NO: 3)
(K) D N E Y R S L I A X X (Q) (Q) (L) X
        (S)                        (E)
        (H)
        (G)

(SEQ ID NO: 4)
(K) (L) (D) (G) F A P K X
    (D) (G) (D)
    (G) (A)
    (A)

(SEQ ID NO: 5)
(K) (H) N E Y R (S) I (L) (A) (K) (P) X (L) (N) X
    (S)            (I) (T)
    (G)

(SEQ ID NO: 6)
(K) X (P) Y (D) X (D) V X A (D) X X X (T) (P) (P) X
      (G) (K) (P)   (T)         (T)
      (D)           (E)

X indicates that no amino acid could be ascribed to that particular position. Residues in brackets are ascribed with less confidence than the other residues. In some cases, it was not possible to differentiate between two or three residues in a particular cycle in which case, they are listed beneath one another. The first residue in each peptide is assumed to be a lysine (K) based on the specificity of Endoproteinase Lys-C.

These sequences are suitable for the design of oligonucleotide sequences which would be suitable to use as hybridisation probes to identify the gene coding for the antigen in gene libraries generated using *H. contortus* RNA (complementary DNA libraries) or DNA (genomic libraries) or as primers for the polymerase chain reaction (PCR).

EXAMPLE 11

Molecular Cloning of the 45 kD gene (a) Oligonucleotide synthesis

From the amino acid sequence described in Example 10, oligonucleotides were prepared that could be used to screen cDNA and genomic libraries to identify the gene(s) encoding the 45 kD antigen. In addition, the oligonucleotide could be used in conjunction with oligo (dT) in PCR (Saiki et al., 1988) to amplify the DNA encoding the 45 kD protein.

The following multiply-degenerate primers were designed and synthesized on an Applied Biosystem Model 380A automated DNA synthesizer. Nucleotides additional to those necessary to encode the required amino acid sequence were included on the 5' ends of the oligonucleotides. These sequences encode sites for the restriction enzymes, *Eco* RI and *Sma* I in order to assist in the cloning of PCR amplified DNA into appropriate vectors. An oligo (dT) primer for use in PCR was also synthesized. The primer also contained *Eco* RI and *Sma* I restriction sites.

A112/301 (SEQ ID NO: 7)
```
GCGAATTCCCGGG.GCA.TTT.CAT. CCG.GGG.AAC.AAC.AAC.GGG.ATG.ACG.GAC.G
                T   C   C   A   A   T   T   A       A   T
                C           T   T               T   T
                            C   C               C   C
```

A112/302 (SEQ ID NO: 8)
```
GCGAATTCCCGGG.GCA.TTT.CAT.CCG.GGG.TCG .AAC.AAC.GGG.ATG.ACG.GAC.G
                T   C   C   A   A AGA  T   T   A       A   T
                C           T   T   T                  T   T
                            C   C   C               C       C
```

A112/302 (SEQ ID No: 8) is identical to A112/301 (SEQ ID No: 7) except for the sixth codon from the 5' end. This was altered from AAC/T to T/AC/GG/A/T/C to account for the mixed signal seen in the amino terminal sequence, viz. asparagine (A112/301SEQ ID No: 7) or serine (A112/302, SEQ ID No: 8).

(b) RNA isolation and cDNA library construction

Total RNA was isolated from 1 g (wet weight) of *H. contortus* using an RNA extraction kit purchased from Pharmacia (Cat #XY-016-00-01). Larvae were obtained from the abomasum of sheep 15 days after infestation with exsheathed L3 stage parasites and stored a –70° C. after snap freezing in liquid nitrogen. In order to extract RNA, the frozen worms were pulverized under liquid nitrogen, added to 7 ml extraction solution (which is a buffered aqueous solution containing guanidine thiocyanate, N-lauryl sarcosine and EDTA; density at 25° C. =1.15 g/ml) and then layered over 2×1.25 ml cushions of CsTFA (buffered aqueous solution containing CsTFA; density at 25° C.=1.51 g/ml) in 13×51 mmpolyallomer tubes. The gradients were centrifuged at 31,000 rpm for 6 hours at 15° C. using an SW 50.1 rotor in an L8-70 Beckman ultracentrifuge. After centrifugation, pellets of RNA were dissolved in TE buffer (10 mM Tris-HCl, pH 7.5, 1 mM EDTA) and reprecipitated from ethanol at –20° C. The sedimented RNA was then dissolved again in TE and further purified by centrifugation through an oligo (dT)-cellulose column (Pharmacia mRNA Purification Kit Cat, # XY-012-00-02) as described by the manufacturer.

The resulting purified poly(A)$^+$RNA was used to construct cDNA libraries using a Pharmacia cDNA Synthesis Kit (Cat # XY-003-00-03). Briefly, polyadenylated RNA purified from 325 µg total RNA was treated with the Moloney Murine Leukaemia Virus Reverse Transcriptase in the presence of oligo (dT)$_{12-18}$. Second strand synthesis was accomplished using RNase H and *E. coli* DNA polymerase I. The double stranded cDNA was treated with the Klenow fragment of DNA polymerase and ligated to *Eco* RI/*Not* I adaptors. The cDNA was then treated with T4 polynucleotide kinase to phosphorylate it and ligated into *Eco* RI digested, dephosphorylated lambda gt 10 arms and packaged in vitro into infectious bacteriophage particles (Protoclone lambda gt 10 System and Packagene System, Promega) as described by the supplier. The packaged cDNA was transfected into *E. coli* C600 Hfl and plated on Luria agar plates using Luria top agar containing 10 mM MgSO$_4$. A total of 6×10$^{7}$ p.f.u. were obtained of which 98% were recombinants. The average insert size was 2.0 kbp.

(c) Preparation of DNA probes for screening recombinant libraries.

A 45 kD antigen-specific double stranded DNA probe was prepared using PCR. The procedure used was based on that described by Saiki et al. (1985) and used a cloned form of *Taq* polymerase (Perkin Elmer Cetus). 2 µg total RNA was annealed to 100 ng oligo (dT) PCR primer in 6 µl water by heating to 70° C. for 5 minutes and then leaving to cool to room temperature. The annealed RNA-oligo (dT) was then incubated with 200 units reverse transcriptase (BRL) in the presence of 50 mM Tris-HCl (pH 8.3), 75 mM KCl, 10 mM MgCl$_2$, 5 mM spermidine, 10 mMDTT, 1 unit RNasin for 1 hour at 37° C. in a final volume of 25 µl. A similar reaction from which reverse transcriptase was omitted served as a negative control for the PCR reaction.

PCR was performed on cDNA produced as described above. The reaction mixture contained first strand cDNA synthesized from 1 µg total RNA, 1 µM each of one of A112/301 (SEQ ID No. 7 or A112/302 (SEQ ID No: 8) and 1 µM oligo (dT) PCR primer, 200 µM of each dNTP, 50 mM KCl, 10 mM Tris-HCl (pH 9.0), 2 mM MgCl$_2$, 0.01% gelatin, 0.01% Triton X-100 and 2 units of *Taq* polymerase in a total volume of 100 µl. Amplification was carried out over 25 cycles, each of which consisted of denaturation for 1 minute at 94° C., annealing for 2 minutes at 40° C. and extension for 3 minutes at 72° C.

Samples of each PCR reaction were analyzed on a 0.8% agarose gel at the end of the reactions.

In the reaction containing primer A112/301 (SEQ ID No: 7) and oligo (dT), a unique band of approximately 650 bp was observed. Several other bands were present but these were also seen in the reaction in which oligo (dT) only was used. The approximately 650 bp band was not seen when primer A112/302 (SEQ No: 8) was used. No bands were seen in the negative control reaction from which reverse transcriptase was omitted.

The approximately 650 bp PCR product was digested with *Eco* RI, purified by electrophoresis on an agarose gel, ligated into pBluescript SK- (Stratagene) using conventional techniques (Maniatis et al., 1982) and sequenced using the dideoxy chain termination procedure (Amersham Microtitre Plate Sequencing Kit, Cat #RPN.1590). Sequence analysis of the ends of the clone confirmed that it contained the sequence of primer A112/301 (SEQ ID No: 7) at the 5' end and a poiy (A) stretch at the 3' end. Furthermore, 14 out of the 18 nucleotides immediately downstream from the 3' end of the region corresponding to the primer A112/301 (SEQ ID No: 7) corresponded to those predicted from the amino acid sequence of the purified protein. This is an homology of 86% at the amino acid level (18 amino acids out of the 21 returned from N terminal sequencing). The differences between the amino acid sequence obtained from the purified antigen and that predicted from the DNA sequence of the PCR clone could be accounted for by ambiguities in the amino terminal sequence analysis of the purified protein and/or PCR incorporation errors although this is an unlikely explanation given the large number of differences. The PCR clone was grown, DNA was isolated, digested with *Eco* RI and the insert purified for use as a hybridisation probe to screen the cDNA library described in (b) of this example.

Approximately 10$^5$ p.f.u. were screened by hybridization of nitrocellulose filter replicas of the library at 55° C. in a solution containing 2×10$^5$ cpm/ml probe, 5×SSPE, 5×Denhardt's solution, 0.5% (w/v) SDS and 20 µg/ml sheared, denatured salmon sperm DNA. After washing the filters at 60° C. in 0.5×SSC, 0.1% SDS and autoradiography, 16 positive plaques were identified. Of these, 8 were picked for subsequent purification and analysis. *Eco* RI inserts were isolated from the purified phage DNA and subcloned into pBluescript SK- for further analysis. The sequence of one of these clones, pBTA879, is shown in FIG. 7 and in SEQ ID No: 9.

There is a single long open reading frame of 1336 nucleotides followed by a translation stop codon, TGA. The open reading frame of this clone extends from the 5' end of the clone. There is no methionine initiation codon present in this region of the sequence so this clone probably does not represent the complete coding region.

Close examination of the amino acid sequence derived from the cDNA sequence (FIG. 7, SEQ ID Nos. 9 and 10 ) reveals a region of homology with the amino terminal sequence of the purified 45 kD protein commmencing at nucleotide 65 from the 5' end of the cDNA clone where 11 of the predicted amino acids occur over the following 16 residues. In addition, there is a second region with homology with the N-terminal sequence commencing at nucleotide 773 of the sequence (SEQ ID No: 9). Of 19 amino acids, 14 residues are identical with those determined from the protein sequence. The level of homology was 73.7% at the amino acid level. It appears that there may be repetitive domains within the molecule. Both of these regions of homology are indicated in FIG. 7 by double underlining.

Other regions within the predicted amino acid sequence which share homology with the Endoproteinase Lys-C peptide sequences derived from the purified protein are indicated in FIG. 7 (by single underlining). These regions all lie within the carboxy-terminal half of the molecule; all in the portion which is carboxy-terminal to amino acid 253 of SEQ ID No: 10.

In addition, there is a region immediately preceding the sequence starting at nucleotide 773 of SEQ ED No: 9 which is similar to peptide sequences which have been hypothesised as being highly susceptible to proteinase digestion.

The amino acid sequence N-terminal to that starting at nucleotide 65 of SEQ ID No: 9 is very hydrophobic and contains amino acids similar to those recognised by signal peptidases.

The most likely explanation of these analyses is that the cDNA clone which is described in FIG. 7 (SEQ ID No: 9) encodes a glycoprotein which is related to, but not identical the native glycoprotein isolated from *H. contortus*. The cDNA clone does not code for the full length protein; at least a complete signal peptide precedes that shown in FIG. 7 (SEQ ID No: 10) and it is possible that further amino acids may also be present in the full-length native molecule.

In order to isolate a cDNA clone coding for the full length native 45 kD antigen, cDNA libraries were screened with the fragment isolated from pBTA879. The cDNA library described in (b) of this example was again screened using the Eco RI band of pBTA 879 as hybridisation probe. Approximately $10^5$ p.f.u. were screened using the same conditions as outlined earlier. After washing the filters at 60° C. in 0.5×SSC, 0.1% SDS and autoradiography, 15 positive plaques were identified. Of these 11 *Eco* RI inserts were purified and subcloned into pBluescript SK- for further analysis. The sequence of one of these clones, pBTA 963, is shown in FIG. 8 and in SEQ ID No: 11. This contains an open reading frame of 1320 nucleotides followed by a translation stop codon, TAA.

Once again, this clone does not contain an initiation methionine, however, 16 out of 18 amino acids coded for by the 5' sequence of this clone are identical to the original N-terminal amino acid sequence (SEQ ID No: 1). This region of homology starts at base 50 of SEQ ID No: 11 or amino acid 12 of SEQ ID No: 12 and a second repeat can be found starting at base 722 of SEQ ID No: 11. Both regions are shown with double underlining. The other peptide sequences (SEQ ID Nos. 2, 3, 4, 5, and 6) can also be located in the translated amino acid sequence from pBTA 963 (SEQ ID Nos. 11 and 12.)These have a much greater homology with the peptide sequences than is seen with pBTA 879 (SEQ ID Nos. 9 and 10). In most cases this homology is 100%.

The other characteristics of the two protein sequences are very similar. Both contain a hydrophobic leader sequence segment, both contain the peptidase sensitive region toward the middle of the molecules and both are of similar molecular weight and overall charge. However, the two share only approximately 54% homology in amino acid sequence overall although the homology is much higher in some places, particularly those from which the peptide sequences were derived.

To try to ensure that the cloned gene codes for the purified antigen, the Eco RI fragment was isolated from the original PCR clone and was inserted into an IPTG inducible bacterial expression vector. The gene product was isolated, purified and used to vaccinate sheep. Sera obtained from these sheep were used to probe Western blots of the purified 45 kD glycoprotein and homogenates of *H. contortus*. In both instances, an antigen with an apparent molecular weight of 45 kD in IEF fractions 1–10 was found to react specifically with the antisera. Antibodies generated against a 24 amino acid long peptide with a sequence predicted from the DNA sequence also reacted with the 45 kD antigen in IEF fractions 1–10.

Close inspection of the Western blots of whole parasite homogenates and each broad range IEF fraction resolved with serum from sheep vaccinated with the recombinant antigen reveals that there are in fact higher molecular weight parasite components which specifically react with the post vaccination serum. These higher molecular weight components are likely to be products of the same gene family to that of the isolated antigen. They are located in IEF fractions 2, 3 and 4 in particular and appear to smear across the isoelectric focussing gels. This phenomenon of not focussing as sharp band upon fractionation by IEF is a characteristic of glycoproteins; the variable carbohydrate residues introduce a heterogeneity of charge on the molecules and a heterogeneity in pI of the population of molecules.

Figure 9:
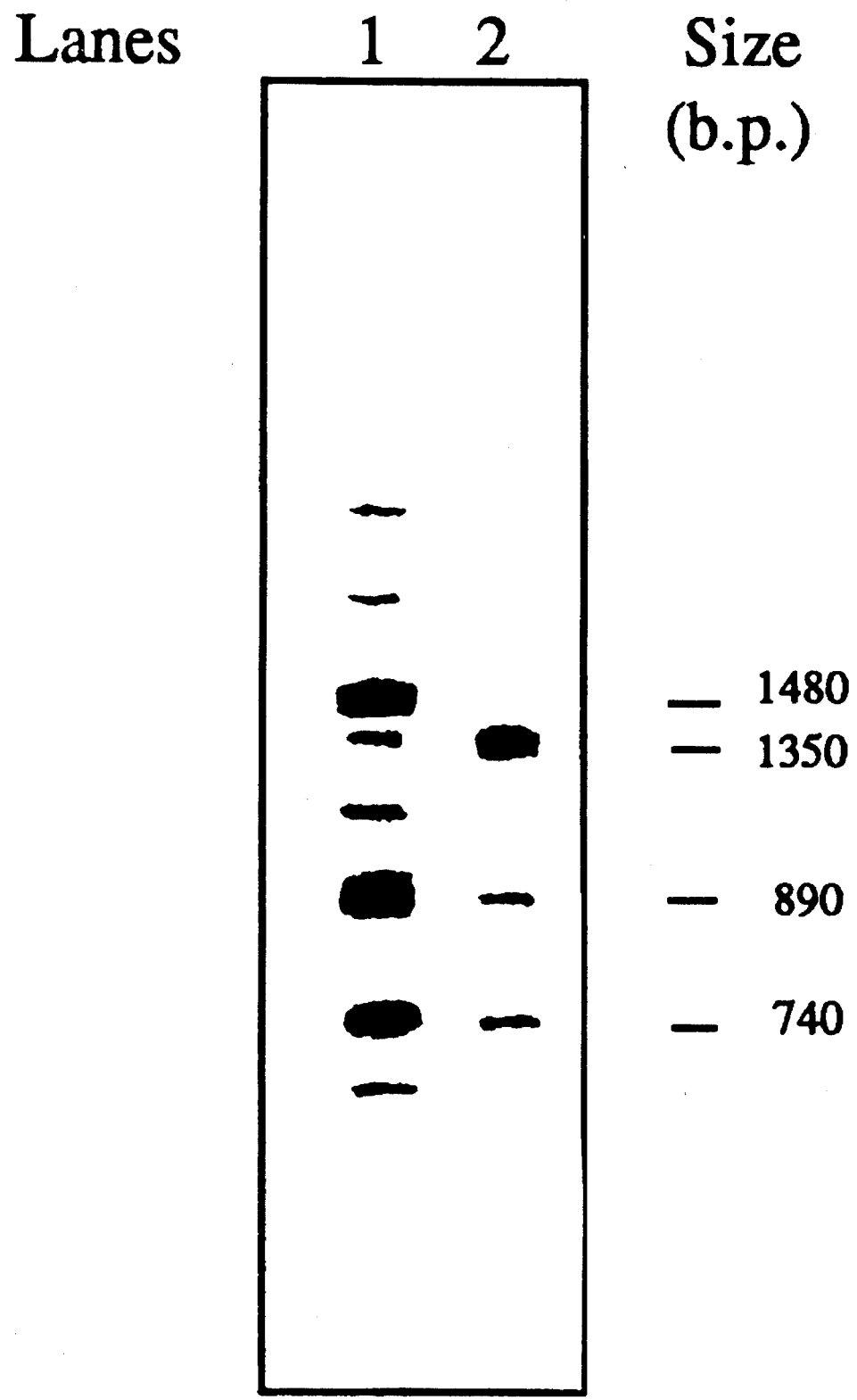
Figure 10:
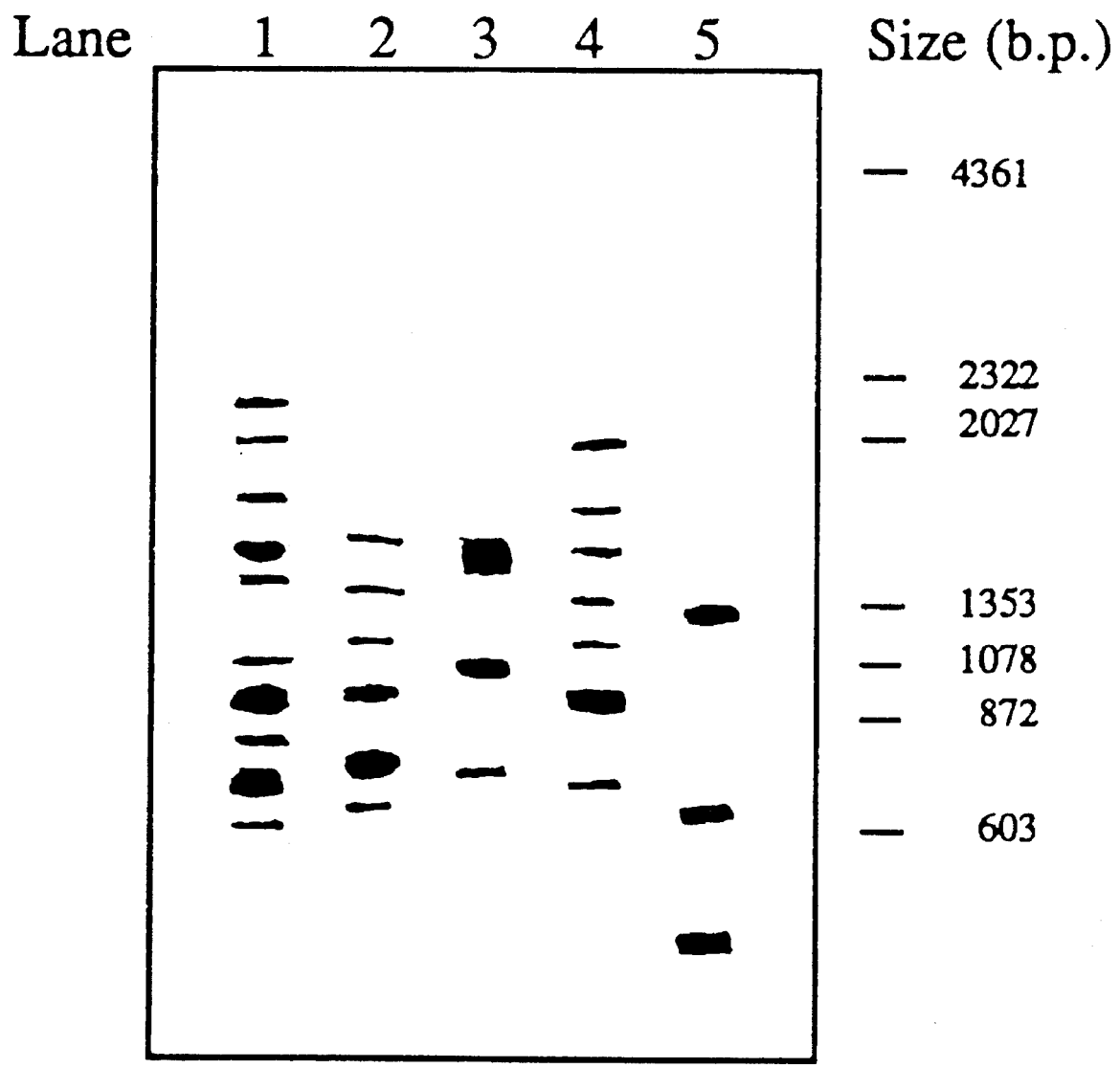

It therefore appears that the native 45 kD antigen isolated from the parasite is a member of a class of proteins which share similar amino acid sequences over portions of the molecules. This is further supported by Southern blot analysis of *H. contortus* genomic DNA using both Eco RI inserts (FIG. 9). These show pBTA 963 hybridising to many bands with varying intensity. The bands at 1480, 890 and 740 base pairs are the most strongly hybridising. The same blot screened with pBTA 879 however lights up a band at 1350 base pairs with the 890 and 740 bands still binding weakly with this probe.

From the Western blots it appears that some members of the protein family may have a molecular weight in excess of 65 kD. It is also possible that the protection afforded to vaccinated sheep and guinea pigs by the IEF fraction 2, 3 and 4 in Examples 4 and 5 of this specification are due to the presence of the larger molecular weight forms of the protective antigen described herein.

No DNA or protein sequences with significant homology to that of this clone could be found after searching the Genbank, EMBL or PIR computer data bases.

EXAMPLE 12

Homologous genes related to that of the protective antigen are present in other species of parasitic nematode DNA hybridisation (or Southern blot analysis) was carried out using standard techniques (Maniatis et al., 982) to determine whether other species of parasitic nematodes have genes which are "homologous" to those coding for the *H. contortus* protective antigen. The *Eco* RI insert of the cDNA clone pBTA963 described in Example 11 (FIG. 8, SEQ ID No: 11) was used as a hybridisation probe to DNA isolated from a number of other species of parasitic nematodes. As well as hybridizing strongly to several restriction fragments in the DNA isolated from the homologous species, i.e., *H. contortus,* as expected, the probe also hybridized to specific restriction fragments in DNA isolated from *Ostertagia circumcincta, Ostertagia ostertagi* and *Trichostrongylus colubriformis.* The blots were washed at a stringency that suggested that the level of homology was about 70%. (FIG. 10).

This clearly demonstrates that there are genes which are closely related to that coding for the protective antigen in these other species of parasitic nematodes and, by extension, in all species of parasitic nematodes. These genes could be isolated using standard molecular biological techniques, and recombinant organisms could be made which synthesise those related or homologous antigens from the other species of parasitic nematode. The present inventors consider that the related antigens will serve as effective immunogens to provide protection to vaccinated animals against infection by the other species of parasite. In addition, related antigens isolated from a broad range of parasitic nematodes could be isolated and provide effective protective immunogens to protect animals against infestation by an extensive range of such nematodes.

It has already been demonstrated that this approach can be successful (International application No. PCT/AU88/00239). That patent application describes how an antigen was purified from an homogenate of *T. colubriformis* based on the ability of that antigen to provide protection to guinea pigs against challenge infections by *T. colubriformis.* Amino acid sequence information was determined for this antigen which enabled the gene coding for the antigen to be isolated from recombinant DNA libraries. The DNA coding for the *T. colubriformis* gene was then used as a hybridisation probe to identify recombinant organisms coding for the "homologous " gene from *H. contortus.* Recombinant organisms were then constructed which synthesised the *H. contortus* antigen which was then used in vaccination and challenge trials in sheep and guinea pigs. The *H. contortus* recombinant antigen provided protection to vaccinated sheep against infestation by *H. contortus* and provided protection to guinea pigs against challenge infection by *I. colubriformis.*

This demonstrates that it is possible, given the DNA sequence homology demonstrated in the above hybridisation experiments, to use the cloned DNA sequence coding for protective antigen from one species of parasitic nematode to identify clones coding for the homologous gene products from other species of parasitic nematodes, engineer those recombinant organisms to express the homologous antigen and use this in a vaccine to provide protection against the other species of parasitic nematode. It is considered that a natural extension of the results presented here is to do so with the DNA sequences of the present invention.

It is to be understood that the nucleotide sequence of the homologous genes and the amino acid sequence of the homologous antigens may not be identical to those of the first target species but will be related by at least 50% over a stretch of at least 60 base pairs and preferably the relationship would be 70% or more over this same region with the homology at the amino acid level being at least 70% over 20 amino acids. In most cases, this degree of homology would be sufficient to enable an unambiguous identification of the relatedness of the two genes or proteins.

EXAMPLE 13

Expression of the 45 kD Antigen in *E. coli*

A number of systems could be used to express the recombinant 45 kD antigen, e.g. mammalian cells, virus-infected insect cells, yeasts, or bacteria. As an example, the gene was expressed in *E. coli.* The full cDNA fragment from pBTA 963 (SEQ ID No: 9) was isolated as a 1386 base pair Bam HI/Hind III fragment, and was subcloned into *E. coli* expression vector pBTA 954. pBTA 954 is a pUR-based vector containing the *lac* promoter, the initiating amino acids for the β-galactosidase gene and multiple cloning sites. When expression was induced by addition of 1 mM IPTG, this yielded a fusion protein with 11 N-terminal amino acids encoded by the vector, fused to the 45 kD protein. The apparent molecular weight of the fusion protein was approximately 61 kD (FIG. 11*a*). The fusion protein was recognised by rabbit serum raised against a peptide corresponding to the truncated N-terminus of the 45 kD protein (FIG. 11*b*). This serum had previously been shown to recognise the dominant protein in the native extract, IEF fraction 1.

The fusion protein could be purified by standard techniques known in the art, formulated with a suitable adjuvant and used to vaccinate the host such as sheep and provide protection against parasite infection.

EXAMPLE 14

Immunological Cross-Reactivity between Antibodies to the 45 kD antigen and *Dirofilaria immitis* proteins Rabbits were vaccinated with a synthetic peptide derived from the sequence of the N-terminal region of the 45 kD antigen. Antisera from these rabbits was used to probe a Western blot of extracts from both adult *D. immitis* and *H. contortus.* After development with a second antibody conjugated to alkaline phosphatase two antigens from each species were shown to be reactive. Components of 45 kD and 27 kD were detected in the *H. contortus* extract and 52 and 32 kD in the D. immitis extract (FIG. 12). This result supports other observations (Example 12) using DNA hybridisation techniques, that proteins related to the 45 kD antigen are present and are expressed in *D. immitis.*

EXAMPLE 15

Scale up of ManufactUring for Commercial Vaccines

The production and purification techniques so far described are carried out at laboratory scale. For commercial production of the antigens of the invention, large scale fermentation of transformed hosts is required.

The large scale fermentations are performed according to standard techniques, the particular techniques selected being appropriate to the transformed host used for production of the antigen.

DEPOSITION OF MICROORGANISMS

Strain BTA 2033, which is *E. coli* JM101 containing the plasmid pBTA 879, has been deposited with Australian Government Analytical Laboratories of 1 Suakin Street, Pymble 2073, New South Wales, Australia in accordance with the provisions of the Budapest Treaty on 29 Jan. 1992 under accession number N92/4387.

The genotype of *E- coli* JM101 is: Δ(pro-lac). F' lacI$^q$ ΔM15, traD1, λ⁻. pBTA 879 is pBLUESCRIPT-SK-minus (Stratagene, San Diego, Calif., USA) containing a 1400 base pair Eco RI insertion coding for a portion of an antigenic protein from the gasto-intestinal nematode,

*Haemonchus contortus.*

Strain BTA 2125, which is *E. coli* SURE strain containing the plasmid pBTA 963, has been deposited with Australian Government Analytical Laboratories of 1 Suakin Street, Pymble 2073, New South Wales, Australia in accordance with the provisions of the Budapest Treaty on 9 Jan. 1992 under accession number N92/4388.

The genotype of *E. coli* SURE is BTA2125 is: *E. coli* SURETM strain (Stratagene, San Diego, Calif., USA), genotype: mcrA, Δ(mrr, hsd RMS mcrBC), endA1, supE44, thi-1, λ⁻, gyrA96, relA1, lac, recB, recJ, sbcC, umuC::Tnr-(kan$^R$), uvrC, {F' proAB, lacI$^q$ ZΔM15, Tn10(tet$^R$)}.

Plasmid pBTA 963 is pBLUESCRIPT-SK-minus (Stratagene, San Diego, Calif., USA), containing a 1386 base pair Eco RI insertion coding for a portion of an antigenic protein from the gastro-intestinal nematode *Haemonchus contortus.*

INDUSTRIAL APPLICATIONS

The present invention is of use in providing antigens, vaccines, and antibodies suitable for protecting animals against infection by parasitic nematodes.

REFERENCES

Maniatis T, Fritsch EF and Sambrook J (eds) (1982) Molecular cloning: A laboratory manual CSH Laboratory, Cold Spring Harbor.

Saiki R. K., Gelfand D. H., Stoffels, Scharf S. J. Higuchi R., Horn G. T., Mullis K. B. and Erlich H. A. (1988) Primer directed amplification of DNA with a thermostable DNA polymerase Science 239: 487–491.

---

We claim:

1. A substantially purified nematode composition, consisting essentially of a protein comprising amino acids 12 to 440 of SEQ ID No. 12.

2. A composition according to claim 1, having a purity of at least 90%.

3. A process for preparing a composition according to claim 1, which process comprises:

a) homogenizing young adults of a parasitic nematode species to produce an homogenate;

b) obtaining membranous material from the homogenate;

c) extracting the membranous material with a buffer containing low levels of a zwitterionic detergent to obtain a detergent extract d) chromatographing the detergent extract on a wheat-germ lectin sepharose column; and e) collection flow-through from the column.

4. The process according to claim 3 which also comprises:

fractionation by preparative iso-electric focusing and collection of fractions having a pI in the range 4.0–4.3;

fractionation by gel filtration chromatography to collect fractions with molecular weights in the range 10–60 kD; and fractionation by lentil lectin or *Helix pommata* lectin chromatography and collecting bound material.

5. The process according to claim 3 which also comprises:

fractionation by preparative iso-electric focussing and collection of fractions having a pI in the range 3.8–4.4, fractionation by gel filtration chromatograhy to collect fractions with molecular weights in the range 10–60 kD; and fractionation by lentil lection or *Helix pomatia* lectin chromatography and collecting bound material.

6. A vaccine comprising an effective amount of the nematode composition of claim 1 together with a pharmaceutically or veterinarally acceptable carrier or diluent.

7. The vaccine of claim 6 further comprising an adjuvant.

8. A method of protecting a host against *Haemonchus contortus* infestation comprising administering to the host an effective amount of the nematode composition of claim 1.

9. A substantially purified nematode composition, consisting essentially of a protein comprising amino acids 17 to 454 of SEQ ID No: 10.

10. An expression product of a transformed host, wherein said transformed host comprises a DNA molecule encoding a nematode protein which comprises amino acids 12 to 440 of (SEQ ID No: 12.

11. An expression product according to claim 10, wherein said expression product is a fusion product.

12. A synthetic polypeptide which comprises amino acids 12 to 440.

13. A vaccine comprising an effective amount of the synthetic polypeptide of claim 12 together with a pharmaceutically or veterinarally acceptable carier or diluent.

14. The vaccine of claim 13 further comprising an adjuvant.

15. A method of protecting a host against *Haemonchus contortus* infestation comprising administering to the host an effective amount of the synthetic polypeptide of claim 12.

* * * * *

UNITED STATES PATENT AND TRADEMARK OFFICE
CERTIFICATE OF CORRECTION

PATENT NO. : 5,525,508
DATED : June 11, 1996
INVENTOR(S) : SHARP et al.

It is certified that error appears in the above-identified patent and that said Letters Patent is hereby corrected as shown below:

Title page,
item [73] Assignees: After "COMMONWEALTH", please insert --SCIENTIFIC--.

In the Claims:

Claim 3, last line, please delete "collection" and insert --collecting--.

Claim 10, last line, should read -- (SEQ ID NO:12) --.

Claim 12, last line, please insert --of SEQ ID No: 12--.

Claim 13, last line, please delete "carier" and insert --carrier--.

Signed and Sealed this

Sixteenth Day of December, 1997

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( v ) FRAGMENT TYPE: N-terminal ( v i ) ORIGINAL SOURCE:
        ( A ) ORGANISM: Haemonchus contortus ( i x ) FEATURE:
        ( A ) NAME/KEY: Modified-site
        ( B ) LOCATION: 2
        ( D ) OTHER INFORMATION: /note="May be Phe or Tyr"

( i x ) FEATURE:
        ( A ) NAME/KEY: Modified-site
        ( B ) LOCATION: 3
        ( D ) OTHER INFORMATION: /note="May be His"

( i x ) FEATURE:
        ( A ) NAME/KEY: Modified-site
        ( B ) LOCATION: 5
        ( D ) OTHER INFORMATION: /note="May be Gly, Asp or Pro"

( i x ) FEATURE:
        ( A ) NAME/KEY: Modified-site
        ( B ) LOCATION: 6
        ( D ) OTHER INFORMATION: /note="May be Ser or Asn"

( i x ) FEATURE:
        ( A ) NAME/KEY: Modified-site
        ( B ) LOCATION: 19
        ( D ) OTHER INFORMATION: /note="May be Val or Ser"

( i x ) FEATURE:
        ( A ) NAME/KEY: Modified-site
        ( B ) LOCATION: 20
        ( D ) OTHER INFORMATION: /note="May be Asp, Gly or Pro"

( i x ) FEATURE:

(A) NAME/KEY: Modified-site
(B) LOCATION: 21
(D) OTHER INFORMATION: /note="May be Lys, Gly, Pro or Asp"

(xi) SEQUENCE DESCRIPTION: SEQ ID NO:1:

Ala Xaa Xaa Pro Xaa Xaa Asn Asn Gly Met Thr Asp Glu Ile Arg Gln
1               5                   10                  15

Ile Phe Xaa Xaa Xaa
            20

(2) INFORMATION FOR SEQ ID NO:2:

(i) SEQUENCE CHARACTERISTICS:
(A) LENGTH: 19 amino acids
(B) TYPE: amino acid
(D) TOPOLOGY: linear (ii) MOLECULE TYPE: peptide (v) FRAGMENT TYPE: N-terminal (vi) ORIGINAL SOURCE:
(A) ORGANISM: Haemonchus contortus (ix) FEATURE:
(A) NAME/KEY: Modified-site
(B) LOCATION: 2..3
(D) OTHER INFORMATION: /note="Amino acids unknown"

(ix) FEATURE:
(A) NAME/KEY: Modified-site
(B) LOCATION: 4
(D) OTHER INFORMATION: /note="May be Pro or Tyr"

(ix) FEATURE:
(A) NAME/KEY: Modified-site
(B) LOCATION: 6
(D) OTHER INFORMATION: /note="Amino acid unknown"

(ix) FEATURE:
(A) NAME/KEY: Modified-site
(B) LOCATION: 17
(D) OTHER INFORMATION: /note="May be Asn or Ser"

(xi) SEQUENCE DESCRIPTION: SEQ ID NO:2:

Lys Xaa Xaa Xaa Asp Xaa Glu Val Glu Ala Asn Thr Ala Ala Tyr Ala
1               5                   10                  15

Xaa Glu Glu (2) INFORMATION FOR SEQ ID NO:3:

(i) SEQUENCE CHARACTERISTICS:
(A) LENGTH: 16 amino acids
(B) TYPE: amino acid
(D) TOPOLOGY: linear (ii) MOLECULE TYPE: peptide (v) FRAGMENT TYPE: N-terminal (vi) ORIGINAL SOURCE:
(A) ORGANISM: Haemonchus contortus (ix) FEATURE:
(A) NAME/KEY: Modified-site
(B) LOCATION: 2
(D) OTHER INFORMATION: /note="May be Asp, Ser, His or Gly"

(ix) FEATURE:
(A) NAME/KEY: Modified-site
(B) LOCATION: 11..12
(D) OTHER INFORMATION: /note="Amino acids unknown"

( i x ) FEATURE:
    ( A ) NAME/KEY: Modified-site
    ( B ) LOCATION: 16
    ( D ) OTHER INFORMATION: /note="Amino acid unknown"

( x i ) SEQUENCE DESCRIPTION: SEQ ID NO:3:

```
Lys  Xaa  Asn  Glu  Tyr  Arg  Ser  Leu  Ile  Ala  Xaa  Xaa  Glx  Gln  Leu  Xaa
 1              5                             10                        15
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Haemonchus contortus ( i x ) FEATURE:
        ( A ) NAME/KEY: Modified-site
        ( B ) LOCATION: 2
        ( D ) OTHER INFORMATION: /note="May be Leu, Asp, Gly or
            Ala"

( i x ) FEATURE:
        ( A ) NAME/KEY: Modified-site
        ( B ) LOCATION: 3
        ( D ) OTHER INFORMATION: /label=RESIDUE-3
            / note="AMINO ACID MAY BE ASP, GLY OR ALA"

( i x ) FEATURE:
        ( A ) NAME/KEY: Modified-site
        ( B ) LOCATION: 4
        ( D ) OTHER INFORMATION: /label=RESIDUE-4
            / note="AMINO ACID MAY BE GLY OR ASP"

( i x ) FEATURE:
        ( A ) NAME/KEY: Modified-site
        ( B ) LOCATION: 9
        ( D ) OTHER INFORMATION: /note="Amino acid unknown"

( x i ) SEQUENCE DESCRIPTION: SEQ ID NO:4:

```
Lys  Xaa  Xaa  Xaa  Phe  Ala  Pro  Lys  Xaa
 1              5
```

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Haemonchus contortus ( i x ) FEATURE:
        ( A ) NAME/KEY: Modified-site
        ( B ) LOCATION: 2
        ( D ) OTHER INFORMATION: /note="May be His, Ser or Gly"

( i x ) FEATURE:
        ( A ) NAME/KEY: Modified-site
        ( B ) LOCATION: 9
        ( D ) OTHER INFORMATION: /note="May be Leu or Ile"

( i x ) FEATURE:

(A) NAME/KEY: Modified-site
(B) LOCATION: 10
(D) OTHER INFORMATION: /note="May be Ala or Thr"

(ix) FEATURE:
(A) NAME/KEY: Modified-site
(B) LOCATION: 13
(D) OTHER INFORMATION: /note="Amino acid unknown"

(ix) FEATURE:
(A) NAME/KEY: Modified-site
(B) LOCATION: 16
(D) OTHER INFORMATION: /note="Amino acid unknown"

(xi) SEQUENCE DESCRIPTION: SEQ ID NO:5:

Lys Xaa Asn Glu Tyr Arg Ser Ile Xaa Xaa Lys Pro Xaa Leu Asn Xaa
1               5                   10                  15

(2) INFORMATION FOR SEQ ID NO:6:

(i) SEQUENCE CHARACTERISTICS:
(A) LENGTH: 18 amino acids
(B) TYPE: amino acid
(D) TOPOLOGY: linear (ii) MOLECULE TYPE: peptide (v) FRAGMENT TYPE: N-terminal (vi) ORIGINAL SOURCE:
(A) ORGANISM: Haemonchus contortus (ix) FEATURE:
(A) NAME/KEY: Modified-site
(B) LOCATION: 2
(D) OTHER INFORMATION: /note="Amino acid unknown"

(ix) FEATURE:
(A) NAME/KEY: Modified-site
(B) LOCATION: 3
(D) OTHER INFORMATION: /note="May be Pro, Gly or Asp"

(ix) FEATURE:
(A) NAME/KEY: Modified-site
(B) LOCATION: 4
(D) OTHER INFORMATION: /note="May be Tyr or Lys"

(ix) FEATURE:
(A) NAME/KEY: Modified-site
(B) LOCATION: 5
(D) OTHER INFORMATION: /note="May be Asp or Pro"

(ix) FEATURE:
(A) NAME/KEY: Modified-site
(B) LOCATION: 6
(D) OTHER INFORMATION: /note="Amino acid unknown"

(ix) FEATURE:
(A) NAME/KEY: Modified-site
(B) LOCATION: 7
(D) OTHER INFORMATION: /note="May be Asp, Thr or Glu"

(ix) FEATURE:
(A) NAME/KEY: Modified-site
(B) LOCATION: 9
(D) OTHER INFORMATION: /note="Amino acid unknown"

(ix) FEATURE:
(A) NAME/KEY: Modified-site
(B) LOCATION: 11
(D) OTHER INFORMATION: /note="May be Asp or Thr"

(ix) FEATURE:
(A) NAME/KEY: Modified-site
(B) LOCATION: 12..14
(D) OTHER INFORMATION: /note="Amino acids unknown"

(ix) FEATURE:

(A) NAME/KEY: Modified-site
(B) LOCATION: 18
(D) OTHER INFORMATION: /note="Amino acid unknown"

(xi) SEQUENCE DESCRIPTION: SEQ ID NO:6:

Lys Xaa Xaa Xaa Xaa Xaa Xaa Val Xaa Ala Xaa Xaa Xaa Xaa Thr Pro
1               5                   10                  15

Pro Xaa (2) INFORMATION FOR SEQ ID NO:7:

(i) SEQUENCE CHARACTERISTICS:
      (A) LENGTH: 50 base pairs
      (B) TYPE: nucleic acid
      (C) STRANDEDNESS: double
      (D) TOPOLOGY: linear (ix) FEATURE:
      (A) NAME/KEY: modified_base
      (B) LOCATION: 16

(ix) FEATURE:
      (A) NAME/KEY: modified_base
      (B) LOCATION: 19

(ix) FEATURE:
      (A) NAME/KEY: modified_base
      (B) LOCATION: 22

(ix) FEATURE:
      (A) NAME/KEY: modified_base
      (B) LOCATION: 25

(ix) FEATURE:
      (A) NAME/KEY: modified_base
      (B) LOCATION: 28

(ix) FEATURE:
      (A) NAME/KEY: modified_base
      (B) LOCATION: 31

(ix) FEATURE:
      (A) NAME/KEY: modified_base
      (B) LOCATION: 34

(ix) FEATURE:
      (A) NAME/KEY: modified_base
      (B) LOCATION: 37

(ix) FEATURE:
      (A) NAME/KEY: modified_base
      (B) LOCATION: 40

(ix) FEATURE:
      (A) NAME/KEY: modified_base
      (B) LOCATION: 46

(ix) FEATURE:
      (A) NAME/KEY: modified_base
      (B) LOCATION: 49

(xi) SEQUENCE DESCRIPTION: SEQ ID NO:7:

GCGAATTCCC GGGGCHTTYC AYCCNGGNAA YAAYAAYGGN ATGACNGAYG    50

(2) INFORMATION FOR SEQ ID NO:8:

(i) SEQUENCE CHARACTERISTICS:
      (A) LENGTH: 50 base pairs
      (B) TYPE: nucleic acid
      (C) STRANDEDNESS: double
      (D) TOPOLOGY: linear (iv) ANTI-SENSE: YES (ix) FEATURE:

(A) NAME/KEY: modified_base
                (B) LOCATION: 16

(ix) FEATURE:
                (A) NAME/KEY: modified_base
                (B) LOCATION: 19

(ix) FEATURE:
                (A) NAME/KEY: modified_base
                (B) LOCATION: 22

(ix) FEATURE:
                (A) NAME/KEY: modified_base
                (B) LOCATION: 25

(ix) FEATURE:
                (A) NAME/KEY: modified_base
                (B) LOCATION: 28

(ix) FEATURE:
                (A) NAME/KEY: modified_base
                (B) LOCATION: 29

(ix) FEATURE:
                (A) NAME/KEY: modified_base
                (B) LOCATION: 30

(ix) FEATURE:
                (A) NAME/KEY: modified_base
                (B) LOCATION: 31

(ix) FEATURE:
                (A) NAME/KEY: modified_base
                (B) LOCATION: 34

(ix) FEATURE:
                (A) NAME/KEY: modified_base
                (B) LOCATION: 37

(ix) FEATURE:
                (A) NAME/KEY: modified_base
                (B) LOCATION: 40

(ix) FEATURE:
                (A) NAME/KEY: modified_base
                (B) LOCATION: 46

(ix) FEATURE:
                (A) NAME/KEY: modified_base
                (B) LOCATION: 49

(xi) SEQUENCE DESCRIPTION: SEQ ID NO:8:

GCGAATTCCC GGGGCHTTYC AYCCNGGNWS NAAYAAYGGV ATGACDGAYG           50

(2) INFORMATION FOR SEQ ID NO:9:

(i) SEQUENCE CHARACTERISTICS:
                (A) LENGTH: 1400 base pairs
                (B) TYPE: nucleic acid
                (C) STRANDEDNESS: double
                (D) TOPOLOGY: unknown (ii) MOLECULE TYPE: cDNA (vi) ORIGINAL SOURCE:
                (A) ORGANISM: Haemonchus contortus (ix) FEATURE:
                (A) NAME/KEY: CDS
                (B) LOCATION: 17..1381

(xi) SEQUENCE DESCRIPTION: SEQ ID NO:9:

GAATTCGCGG CCGCTT ACG ATT GCC TGC TTG GTT CTT CTG GCG CCA TTA   49
                Thr Ile Ala Cys Leu Val Leu Leu Ala Pro Leu
                 1               5                  10

TGG GCG GCT GAT AAG TAT GTG ATT TGT CCT TCT GAC AAT GGC ATG ACA  97

|  |  |  |  |  |  |  |  |  |  |  |  |  |  |  |  |  |
|---|---|---|---|---|---|---|---|---|---|---|---|---|---|---|---|---|
| Trp | Ala | Ala | Asp | Lys | Tyr | Val | Ile | Cys | Pro | Ser | Asp | Asn | Gly | Met | Thr |  |
|  |  |  | 15 |  |  |  |  | 20 |  |  |  |  | 25 |  |  |  |

```
AAT GAA GTT AGA AAT ATG TTC GTT GAT ACG CAC AAT AAA CTC CGA TCG     145
Asn Glu Val Arg Asn Met Phe Val Asp Thr His Asn Lys Leu Arg Ser
        30              35                  40

CAG ACT GCT CAA GGA AAG GCT AAG AAC GCA TTC GGT GGA TTT GCT CCA     193
Gln Thr Ala Gln Gly Lys Ala Lys Asn Ala Phe Gly Gly Phe Ala Pro
    45              50                  55

AAA GCA GCT CGA ATG TTA AAA GTG AGT TAT GAT TGC GAC ATG GAA GCT     241
Lys Ala Ala Arg Met Leu Lys Val Ser Tyr Asp Cys Asp Met Glu Ala
60              65                  70                      75

AAC ATG ATG AAA TGG GCA AAG CAG TGT CAT TTC TAT CAC CCT CCA CCC     289
Asn Met Met Lys Trp Ala Lys Gln Cys His Phe Tyr His Pro Pro Pro
                80                  85                  90

GCA TAT AGG AAC TAC TGG GGA CAA AAT ATT TAT ATG GTG GGA GAT CGA     337
Ala Tyr Arg Asn Tyr Trp Gly Gln Asn Ile Tyr Met Val Gly Asp Arg
            95                  100                 105

TAC TAC AAT TTC ACC TGG CCG TCA ATT GCA GAA ACG GCC GTC ATA TCA     385
Tyr Tyr Asn Phe Thr Trp Pro Ser Ile Ala Glu Thr Ala Val Ile Ser
        110                 115                 120

TGG TGG CAG GAG TTA CAG GTT TTT GGT GTT CCA GAG AAC AAT ATC GTA     433
Trp Trp Gln Glu Leu Gln Val Phe Gly Val Pro Glu Asn Asn Ile Val
125                 130                 135

GTC GCG CCA GAT GAA CAC AAA ACT GGT CAC TAC ATG CAG GTG GTC TGG     481
Val Ala Pro Asp Glu His Lys Thr Gly His Tyr Met Gln Val Val Trp
140                 145                 150                 155

CAA TGG ACC TAC AAA ATT GGT TGC GCA ATT AAT TAT TGC ACA ATA AAC     529
Gln Trp Thr Tyr Lys Ile Gly Cys Ala Ile Asn Tyr Cys Thr Ile Asn
                160                 165                 170

AAG CCA TGG CCA TGG ACA ATC GCA GGA TGC AAC TAT AAC CCT GGT GGT     577
Lys Pro Trp Pro Trp Thr Ile Ala Gly Cys Asn Tyr Asn Pro Gly Gly
            175                 180                 185

GAT AAT GCT TAT TGG GTG GTC TAC GAG ATG GGA GAT CCA TGC ACA ACT     625
Asp Asn Ala Tyr Trp Val Val Tyr Glu Met Gly Asp Pro Cys Thr Thr
        190                 195                 200

GAC GCC GAC TGC AAA TGT GCT GGT TGC GTT TGC AGC CAA GAA GAG GCC     673
Asp Ala Asp Cys Lys Cys Ala Gly Cys Val Cys Ser Gln Glu Glu Ala
205                 210                 215

CTT TGC ATT CCG CCA GAA TAC ACT CCC CTT CCA CCT ACT ACC ACT TCA     721
Leu Cys Ile Pro Pro Glu Tyr Thr Pro Leu Pro Pro Thr Thr Thr Ser
220                 225                 230                 235

ACC ACA ACA CCG AAG CCA ACT ACA ACA ACC GTT GGG GTA CCT AAT         769
Thr Thr Thr Pro Lys Pro Thr Thr Thr Thr Val Gly Val Pro Asn
                240                 245                 250

GCT GGG TCG TGC CCT GAA CTT AAC AAT GGA ATG ACT GAC GAA GCT AGG     817
Ala Gly Ser Cys Pro Glu Leu Asn Asn Gly Met Thr Asp Glu Ala Arg
            255                 260                 265

AAG ATG TTT GTC GAC AAA CAT AAT GAA TAC CGA TCG CTC ATT GCT AAA     865
Lys Met Phe Val Asp Lys His Asn Glu Tyr Arg Ser Leu Ile Ala Lys
        270                 275                 280

GGG CAA GCC AAG GGT AAA CCT GGA CAA TTC GCC CCA AAG GCT GCC AGA     913
Gly Gln Ala Lys Gly Lys Pro Gly Gln Phe Ala Pro Lys Ala Ala Arg
285                 290                 295

ATG ATG AAA GTG AAC TAC GAT TGC GAT GTT GAA GCA AAT GCA ATG GAA     961
Met Met Lys Val Asn Tyr Asp Cys Asp Val Glu Ala Asn Ala Met Glu
300                 305                 310                 315

TGG TCC AAG ACT TGC ACA TTT GGA CTC AAC ACT GCT GCG ATG TTA AAG    1009
Trp Ser Lys Thr Cys Thr Phe Gly Leu Asn Thr Ala Ala Met Leu Lys
                320                 325                 330

CGA TGG GGG AAT AAC ATG CAC ATG ATG TCG TCC AAG GCT AAT AAC AAG    1057
```

```
        Arg  Trp  Gly  Asn  Asn  Met  His  Met  Met  Ser  Ser  Lys  Ala  Asn  Asn  Lys
                       335                 340                      345

ACA  GAG  GCT  GCA  GCT  GAG  GCC  GTC  GCA  GCC  TGG  TTC  GGT  GAT  TTA  CAA     1105
        Thr  Glu  Ala  Ala  Ala  Glu  Ala  Val  Ala  Ala  Trp  Phe  Gly  Asp  Leu  Gln
                       350                 355                      360

AAA  TAT  GGC  GTA  CCT  GAG  AAT  AAC  GTC  TTC  ACG  ATG  AAC  GTT  TAC  ACG     1153
        Lys  Tyr  Gly  Val  Pro  Glu  Asn  Asn  Val  Phe  Thr  Met  Asn  Val  Tyr  Thr
                  365                      370                 375

ACT  TTA  AGT  AAA  TAC  AGT  CAG  TTA  GCG  TGG  CAA  TCG  AGC  GAC  AGA  ATT     1201
        Thr  Leu  Ser  Lys  Tyr  Ser  Gln  Leu  Ala  Trp  Gln  Ser  Ser  Asp  Arg  Ile
        380                      385                 390                           395

GGT  TGT  GTA  GTT  GTA  CCT  TGT  TGG  AGC  TCA  TGG  ACG  GTT  GTG  GTG  TGT     1249
        Gly  Cys  Val  Val  Val  Pro  Cys  Trp  Ser  Ser  Trp  Thr  Val  Val  Val  Cys
                            400                 405                      410

GAA  TAC  AAT  CCC  GGA  GGA  GAC  CTG  CCT  GGC  GAG  GCT  ATC  TAT  GAC  GTA     1297
        Glu  Tyr  Asn  Pro  Gly  Gly  Asp  Leu  Pro  Gly  Glu  Ala  Ile  Tyr  Asp  Val
                       415                 420                      425

GGA  GAT  CCC  TGT  ACG  AAA  GAC  GCC  GAC  TGT  CAG  TGC  CCC  GGC  TGC  ACC     1345
        Gly  Asp  Pro  Cys  Thr  Lys  Asp  Ala  Asp  Cys  Gln  Cys  Pro  Gly  Cys  Thr
                  430                      435                 440

TGT  AGC  AGA  GAT  GAG  GGC  CTT  TGC  GTT  GCT  CCA  TGAACACTGG CGGCCGCTTA       1398
        Cys  Ser  Arg  Asp  Glu  Gly  Leu  Cys  Val  Ala  Pro
             445                      450                 455

AG                                                                                 1400
```

( 2 ) INFORMATION FOR SEQ ID NO:10:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
        Thr  Ile  Ala  Cys  Leu  Val  Leu  Leu  Ala  Pro  Leu  Trp  Ala  Ala  Asp  Lys
         1              5                        10                      15

Tyr  Val  Ile  Cys  Pro  Ser  Asp  Asn  Gly  Met  Thr  Asn  Glu  Val  Arg  Asn
                       20                      25                       30

Met  Phe  Val  Asp  Thr  His  Asn  Lys  Leu  Arg  Ser  Gln  Thr  Ala  Gln  Gly
                  35                      40                       45

Lys  Ala  Lys  Asn  Ala  Phe  Gly  Gly  Phe  Ala  Pro  Lys  Ala  Ala  Arg  Met
             50                       55                      60

Leu  Lys  Val  Ser  Tyr  Asp  Cys  Asp  Met  Glu  Ala  Asn  Met  Met  Lys  Trp
        65                       70                      75                       80

Ala  Lys  Gln  Cys  His  Phe  Tyr  His  Pro  Pro  Pro  Ala  Tyr  Arg  Asn  Tyr
                            85                      90                       95

Trp  Gly  Gln  Asn  Ile  Tyr  Met  Val  Gly  Asp  Arg  Tyr  Tyr  Asn  Phe  Thr
                       100                     105                      110

Trp  Pro  Ser  Ile  Ala  Glu  Thr  Ala  Val  Ile  Ser  Trp  Trp  Gln  Glu  Leu
                  115                     120                      125

Gln  Val  Phe  Gly  Val  Pro  Glu  Asn  Asn  Ile  Val  Val  Ala  Pro  Asp  Glu
             130                     135                      140

His  Lys  Thr  Gly  His  Tyr  Met  Gln  Val  Val  Trp  Gln  Trp  Thr  Tyr  Lys
        145                     150                      155                     160

Ile  Gly  Cys  Ala  Ile  Asn  Tyr  Cys  Thr  Ile  Asn  Lys  Pro  Trp  Pro  Trp
                            165                     170                      175

Thr  Ile  Ala  Gly  Cys  Asn  Tyr  Asn  Pro  Gly  Gly  Asp  Asn  Ala  Tyr  Trp
                       180                     185                      190
```

| | | | | | | | | | | | | | | |
|---|---|---|---|---|---|---|---|---|---|---|---|---|---|---|
| Val | Val | Tyr | Glu | Met | Gly | Asp | Pro | Cys | Thr | Thr | Asp | Ala | Asp | Cys | Lys |
| | | 195 | | | | 200 | | | | | 205 | | | |
| Cys | Ala | Gly | Cys | Val | Cys | Ser | Gln | Glu | Ala | Leu | Cys | Ile | Pro | Pro |
| | 210 | | | | 215 | | | | 220 | | | | | |
| Glu | Tyr | Thr | Pro | Leu | Pro | Pro | Thr | Thr | Thr | Ser | Thr | Thr | Thr | Pro | Lys |
| 225 | | | | | 230 | | | | 235 | | | | | 240 |
| Pro | Thr | Thr | Thr | Thr | Thr | Val | Gly | Val | Pro | Asn | Ala | Gly | Ser | Cys | Pro |
| | | | 245 | | | | | 250 | | | | 255 | | |
| Glu | Leu | Asn | Asn | Gly | Met | Thr | Asp | Glu | Ala | Arg | Lys | Met | Phe | Val | Asp |
| | | | 260 | | | | 265 | | | | | 270 | | |
| Lys | His | Asn | Glu | Tyr | Arg | Ser | Leu | Ile | Ala | Lys | Gly | Gln | Ala | Lys | Gly |
| | | 275 | | | | 280 | | | | | 285 | | | |
| Lys | Pro | Gly | Gln | Phe | Ala | Pro | Lys | Ala | Ala | Arg | Met | Met | Lys | Val | Asn |
| | | 290 | | | 295 | | | | | 300 | | | | |
| Tyr | Asp | Cys | Asp | Val | Glu | Ala | Asn | Ala | Met | Glu | Trp | Ser | Lys | Thr | Cys |
| 305 | | | | 310 | | | | | 315 | | | | | 320 |
| Thr | Phe | Gly | Leu | Asn | Thr | Ala | Ala | Met | Leu | Lys | Arg | Trp | Gly | Asn | Asn |
| | | | 325 | | | | | 330 | | | | | 335 | |
| Met | His | Met | Met | Ser | Ser | Lys | Ala | Asn | Asn | Lys | Thr | Glu | Ala | Ala | Ala |
| | | | 340 | | | | | 345 | | | | 350 | | |
| Glu | Ala | Val | Ala | Ala | Trp | Phe | Gly | Asp | Leu | Gln | Lys | Tyr | Gly | Val | Pro |
| | | 355 | | | | | 360 | | | | | 365 | | |
| Glu | Asn | Asn | Val | Phe | Thr | Met | Asn | Val | Tyr | Thr | Thr | Leu | Ser | Lys | Tyr |
| | 370 | | | | | 375 | | | | | 380 | | | |
| Ser | Gln | Leu | Ala | Trp | Gln | Ser | Ser | Asp | Arg | Ile | Gly | Cys | Val | Val | Val |
| 385 | | | | | 390 | | | | | 395 | | | | 400 |
| Pro | Cys | Trp | Ser | Ser | Trp | Thr | Val | Val | Val | Cys | Glu | Tyr | Asn | Pro | Gly |
| | | | | 405 | | | | | 410 | | | | | 415 |
| Gly | Asp | Leu | Pro | Gly | Glu | Ala | Ile | Tyr | Asp | Val | Gly | Asp | Pro | Cys | Thr |
| | | | 420 | | | | | 425 | | | | | 430 | |
| Lys | Asp | Ala | Asp | Cys | Gln | Cys | Pro | Gly | Cys | Thr | Cys | Ser | Arg | Asp | Glu |
| | | 435 | | | | | 440 | | | | | 445 | | |
| Gly | Leu | Cys | Val | Ala | Pro | | | | | | | | | | |
| | 450 | | | | | | | | | | | | | | |

( 2 ) INFORMATION FOR SEQ ID NO:11:

( i ) SEQUENCE CHARACTERISTICS:
        ( A ) LENGTH: 1386 base pairs
        ( B ) TYPE: nucleic acid
        ( C ) STRANDEDNESS: double
        ( D ) TOPOLOGY: unknown ( i i ) MOLECULE TYPE: cDNA ( v i ) ORIGINAL SOURCE:
        ( A ) ORGANISM: Haemonchus contortus ( i x ) FEATURE:
        ( A ) NAME/KEY: CDS
        ( B ) LOCATION: 17..1339

( x i ) SEQUENCE DESCRIPTION: SEQ ID NO:11:

```
GAATTCGCGG CCGCTT TCG GTG CTT CTG ACG CCA TCA TGC CTG AAA GCC           49
               Ser Val Leu Leu Thr Pro Ser Cys Leu Lys Ala
                1               5                      10

GCG TTT TGC CCC ACA TCG GAC AAT GGC ATG ACC GAT GAA ATT AGG CAG         97
Ala Phe Cys Pro Thr Ser Asp Asn Gly Met Thr Asp Glu Ile Arg Gln
         15                  20                  25
```

| | | | | | | | | | | | | | | | | |
|---|---|---|---|---|---|---|---|---|---|---|---|---|---|---|---|---|
| ATT | TTC | GTT | GAT | AAG | CAC | AAT | GAG | TAT | CGA | TCT | ATT | ATT | GCT | AAA | GGA | 145 |
| Ile | Phe | Val | Asp | Lys | His | Asn | Glu | Tyr | Arg | Ser | Ile | Ile | Ala | Lys | Gly | |
| | | 30 | | | | 35 | | | | | | 40 | | | | |
| CAG | GCC | AAG | AAT | AAA | CTT | GGA | GGA | TTC | GCT | CCG | AAA | GCA | GCT | CGA | ATG | 193 |
| Gln | Ala | Lys | Asn | Lys | Leu | Gly | Gly | Phe | Ala | Pro | Lys | Ala | Ala | Arg | Met | |
| | 45 | | | | | 50 | | | | | 55 | | | | | |
| TTG | AAA | GTG | GGT | TAC | GAT | TGC | GAA | GTT | GAG | GCA | AAT | ACG | GCG | GCA | TAT | 241 |
| Leu | Lys | Val | Gly | Tyr | Asp | Cys | Glu | Val | Glu | Ala | Asn | Thr | Ala | Ala | Tyr | |
| 60 | | | | | 65 | | | | | 70 | | | | | 75 | |
| GCA | AAA | GAG | TGC | AAG | TTC | GAA | CAT | GAT | CCA | CCC | GAG | CAA | AGG | AAT | TAT | 289 |
| Ala | Lys | Glu | Cys | Lys | Phe | Glu | His | Asp | Pro | Pro | Glu | Gln | Arg | Asn | Tyr | |
| | | | | 80 | | | | | 85 | | | | | 90 | | |
| TGG | GGG | CAG | AAC | CTG | TGG | ATG | CTA | GGA | GGG | ACT | AAT | TAC | AGC | AAG | ACG | 337 |
| Trp | Gly | Gln | Asn | Leu | Trp | Met | Leu | Gly | Gly | Thr | Asn | Tyr | Ser | Lys | Thr | |
| | | | 95 | | | | | 100 | | | | | 105 | | | |
| GAA | TCT | GCA | AAA | TTA | AGT | GTC | CAA | GCT | TGG | TAC | TGG | GAA | TTG | AAG | ATG | 385 |
| Glu | Ser | Ala | Lys | Leu | Ser | Val | Gln | Ala | Trp | Tyr | Trp | Glu | Leu | Lys | Met | |
| | | 110 | | | | | 115 | | | | | 120 | | | | |
| TTT | GGA | GTG | CCC | GAT | GAA | AAT | ATC | CTG | ACA | ATG | GAA | GTC | TTC | GAT | CGG | 433 |
| Phe | Gly | Val | Pro | Asp | Glu | Asn | Ile | Leu | Thr | Met | Glu | Val | Phe | Asp | Arg | |
| | 125 | | | | | 130 | | | | | 135 | | | | | |
| GGT | GTT | GGC | CAC | TAC | ACA | CAG | GTA | GCC | TGG | CAG | TCT | AGC | GAC | AAA | ATC | 481 |
| Gly | Val | Gly | His | Tyr | Thr | Gln | Val | Ala | Trp | Gln | Ser | Ser | Asp | Lys | Ile | |
| 140 | | | | | 145 | | | | | 150 | | | | | 155 | |
| GGC | TGC | GCA | GTT | GAA | TGG | TGC | CCA | ACC | ATG | ACA | CTT | GTA | GCA | TGC | GAG | 529 |
| Gly | Cys | Ala | Val | Glu | Trp | Cys | Pro | Thr | Met | Thr | Leu | Val | Ala | Cys | Glu | |
| | | | | 160 | | | | | 165 | | | | | 170 | | |
| TAC | AAC | CCT | GCA | GGA | AAT | AGG | ATC | AAT | CAT | TAT | ATT | TAC | GAC | ATC | GGA | 577 |
| Tyr | Asn | Pro | Ala | Gly | Asn | Arg | Ile | Asn | His | Tyr | Ile | Tyr | Asp | Ile | Gly | |
| | | | 175 | | | | | 180 | | | | | 185 | | | |
| GAT | CCA | TGC | ACA | ACT | GAT | GAA | GAC | TGT | CAA | TGC | ACT | GGC | TGC | ACT | TGT | 625 |
| Asp | Pro | Cys | Thr | Thr | Asp | Glu | Asp | Cys | Gln | Cys | Thr | Gly | Cys | Thr | Cys | |
| | | 190 | | | | | 195 | | | | | 200 | | | | |
| AGT | AAA | GAT | GAG | GCC | CTT | TGT | ATT | CCT | CCA | GGA | TAT | ACT | ACC | GTC | ATG | 673 |
| Ser | Lys | Asp | Glu | Ala | Leu | Cys | Ile | Pro | Pro | Gly | Tyr | Thr | Thr | Val | Met | |
| | 205 | | | | | 210 | | | | | 215 | | | | | |
| CCA | CCG | ACT | ACA | GAG | AAA | CCT | ACT | ACA | ACA | CCT | AAA | ATA | TAC | CAT | CCA | 721 |
| Pro | Pro | Thr | Thr | Glu | Lys | Pro | Thr | Thr | Thr | Pro | Lys | Ile | Tyr | His | Pro | |
| 220 | | | | | 225 | | | | | 230 | | | | | 235 | |
| GGT | GGG | ATG | TGC | CCT | GAG | AAT | AAT | AAC | GGA | ATG | ACA | GAT | GAA | GCT | AGG | 769 |
| Gly | Gly | Met | Cys | Pro | Glu | Asn | Asn | Asn | Gly | Met | Thr | Asp | Glu | Ala | Arg | |
| | | | | 240 | | | | | 245 | | | | | 250 | | |
| CAG | ATG | TTC | GTC | GAC | AAA | CAC | AAT | GAG | TAT | CGA | TCC | CTC | ATA | GCT | AAA | 817 |
| Gln | Met | Phe | Val | Asp | Lys | His | Asn | Glu | Tyr | Arg | Ser | Leu | Ile | Ala | Lys | |
| | | | 255 | | | | | 260 | | | | | 265 | | | |
| GGA | CTA | GCT | CAT | AAC | AAT | CTT | GGA | GGG | TTT | GCT | CCA | AAA | GCG | GCT | AGA | 865 |
| Gly | Leu | Ala | His | Asn | Asn | Leu | Gly | Gly | Phe | Ala | Pro | Lys | Ala | Ala | Arg | |
| | | 270 | | | | | 275 | | | | | 280 | | | | |
| ATG | ATG | AAA | GTG | AGC | TAC | AAT | TGC | GAA | ATC | GAA | GCG | AAT | CGA | GTG | GAG | 913 |
| Met | Met | Lys | Val | Ser | Tyr | Asn | Cys | Glu | Ile | Glu | Ala | Asn | Arg | Val | Glu | |
| | 285 | | | | | 290 | | | | | 295 | | | | | |
| TGG | GCG | AAG | GAT | TGC | ACG | CTT | GGG | TAC | AAC | TCT | GTT | GCT | CAA | AAT | AAC | 961 |
| Trp | Ala | Lys | Asp | Cys | Thr | Leu | Gly | Tyr | Asn | Ser | Val | Ala | Gln | Asn | Asn | |
| 300 | | | | | 305 | | | | | 310 | | | | | 315 | |
| CAA | TGG | GGT | TAT | AAT | GTA | CAT | TCA | CTA | CTG | CCG | CAT | ATT | AAC | AAG | ACG | 1009 |
| Gln | Trp | Gly | Tyr | Asn | Val | His | Ser | Leu | Leu | Pro | His | Ile | Asn | Lys | Thr | |
| | | | | 320 | | | | | 325 | | | | | 330 | | |
| GTA | GCA | GCA | GCA | GAG | AGT | GTC | GAG | GCC | TGG | TTC | AAT | GAA | CTA | CAG | ACA | 1057 |
| Val | Ala | Ala | Ala | Glu | Ser | Val | Glu | Ala | Trp | Phe | Asn | Glu | Leu | Gln | Thr | |
| | | | 335 | | | | | 340 | | | | | 345 | | | |

```
TAT  GGT  GCA  CCT  CAG  GAT  AAC  GTT  TTC  AGT  ATG  GAG  GTT  TTC  AAT  CAA      1105
Tyr  Gly  Ala  Pro  Gln  Asp  Asn  Val  Phe  Ser  Met  Glu  Val  Phe  Asn  Gln
          350                355                     360

AAC  GTA  ATA  CAG  GAA  TAC  GCT  CAG  TTG  GCG  TGG  CAA  TCG  AGC  AAC  CAG      1153
Asn  Val  Ile  Gln  Glu  Tyr  Ala  Gln  Leu  Ala  Trp  Gln  Ser  Ser  Asn  Gln
     365                370                     375

ATT  GGT  TGT  GGA  ATT  TTT  TCT  TGC  TGG  GGT  GGC  GCC  TCT  ACA  TTT  GTG      1201
Ile  Gly  Cys  Gly  Ile  Phe  Ser  Cys  Trp  Gly  Gly  Ala  Ser  Thr  Phe  Val
380                     385                     390                          395

GCT  TGC  GAA  TAC  AAT  CCT  GGA  GGA  AAC  TTC  ATC  GGC  GAA  TTG  ATT  TAT      1249
Ala  Cys  Glu  Tyr  Asn  Pro  Gly  Gly  Asn  Phe  Ile  Gly  Glu  Leu  Ile  Tyr
                    400                     405                     410

ACG  ATG  GGA  GAT  CCG  TGC  TCA  ACT  GAC  GAA  GAC  TGT  CAG  TGC  GCT  GGT      1297
Thr  Met  Gly  Asp  Pro  Cys  Ser  Thr  Asp  Glu  Asp  Cys  Gln  Cys  Ala  Gly
               415                     420                     425

TGC  GTC  TGT  AGC  AAA  GAT  GAA  GCA  CTC  TGT  ATT  GCT  CCT  TAAATGCTTG         1346
Cys  Val  Cys  Ser  Lys  Asp  Glu  Ala  Leu  Cys  Ile  Ala  Pro
          430                     435                     440

TGCAATAAAT  CTTCAGTGAA  AGAAAAGCGG  CCGCGAATTC                                       1386
```

( 2 ) INFORMATION FOR SEQ ID NO:12:

( i ) SEQUENCE CHARACTERISTICS:
        ( A ) LENGTH: 440 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Ser  Val  Leu  Leu  Thr  Pro  Ser  Cys  Leu  Lys  Ala  Ala  Phe  Cys  Pro  Thr
  1             5                    10                         15

Ser  Asp  Asn  Gly  Met  Thr  Asp  Glu  Ile  Arg  Gln  Ile  Phe  Val  Asp  Lys
               20                    25                         30

His  Asn  Glu  Tyr  Arg  Ser  Ile  Ile  Ala  Lys  Gly  Gln  Ala  Lys  Asn  Lys
          35                     40                    45

Leu  Gly  Gly  Phe  Ala  Pro  Lys  Ala  Ala  Arg  Met  Leu  Lys  Val  Gly  Tyr
     50                    55                     60

Asp  Cys  Glu  Val  Glu  Ala  Asn  Thr  Ala  Ala  Tyr  Ala  Lys  Glu  Cys  Lys
 65                        70                    75                         80

Phe  Glu  His  Asp  Pro  Pro  Glu  Gln  Arg  Asn  Tyr  Trp  Gly  Gln  Asn  Leu
                    85                     90                         95

Trp  Met  Leu  Gly  Gly  Thr  Asn  Tyr  Ser  Lys  Thr  Glu  Ser  Ala  Lys  Leu
               100                   105                   110

Ser  Val  Gln  Ala  Trp  Tyr  Trp  Glu  Leu  Lys  Met  Phe  Gly  Val  Pro  Asp
          115                   120                   125

Glu  Asn  Ile  Leu  Thr  Met  Glu  Val  Phe  Asp  Arg  Gly  Val  Gly  His  Tyr
     130                   135                   140

Thr  Gln  Val  Ala  Trp  Gln  Ser  Ser  Asp  Lys  Ile  Gly  Cys  Ala  Val  Glu
145                    150                   155                        160

Trp  Cys  Pro  Thr  Met  Thr  Leu  Val  Ala  Cys  Glu  Tyr  Asn  Pro  Ala  Gly
               165                   170                   175

Asn  Arg  Ile  Asn  His  Tyr  Ile  Tyr  Asp  Ile  Gly  Asp  Pro  Cys  Thr  Thr
               180                   185                   190

Asp  Glu  Asp  Cys  Gln  Cys  Thr  Gly  Cys  Thr  Cys  Ser  Lys  Asp  Glu  Ala
          195                   200                   205

Leu  Cys  Ile  Pro  Pro  Gly  Tyr  Thr  Thr  Val  Met  Pro  Pro  Thr  Thr  Glu
     210                   215                   220
```

| | | | | | | | | | | | | | | |
|---|---|---|---|---|---|---|---|---|---|---|---|---|---|---|
| Lys 225 | Pro | Thr | Thr | Thr | Pro 230 | Lys | Ile | Tyr | His | Pro 235 | Gly | Gly | Met | Cys | Pro 240 |
| Glu | Asn | Asn | Asn | Gly 245 | Met | Thr | Asp | Glu | Ala 250 | Arg | Gln | Met | Phe | Val 255 | Asp |
| Lys | His | Asn | Glu 260 | Tyr | Arg | Ser | Leu | Ile 265 | Ala | Lys | Gly | Leu | Ala 270 | His | Asn |
| Asn | Leu | Gly 275 | Gly | Phe | Ala | Pro | Lys 280 | Ala | Ala | Arg | Met | Met 285 | Lys | Val | Ser |
| Tyr | Asn 290 | Cys | Glu | Ile | Glu | Ala 295 | Asn | Arg | Val | Glu | Trp 300 | Ala | Lys | Asp | Cys |
| Thr 305 | Leu | Gly | Tyr | Asn | Ser 310 | Val | Ala | Gln | Asn | Asn 315 | Gln | Trp | Gly | Tyr | Asn 320 |
| Val | His | Ser | Leu | Leu 325 | Pro | His | Ile | Asn | Lys 330 | Thr | Val | Ala | Ala | Ala 335 | Glu |
| Ser | Val | Glu | Ala 340 | Trp | Phe | Asn | Glu | Leu 345 | Gln | Thr | Tyr | Gly | Ala 350 | Pro | Gln |
| Asp | Asn | Val 355 | Phe | Ser | Met | Glu | Val 360 | Phe | Asn | Gln | Asn | Val 365 | Ile | Gln | Glu |
| Tyr | Ala 370 | Gln | Leu | Ala | Trp | Gln 375 | Ser | Ser | Asn | Gln | Ile 380 | Gly | Cys | Gly | Ile |
| Phe 385 | Ser | Cys | Trp | Gly | Gly 390 | Ala | Ser | Thr | Phe | Val 395 | Ala | Cys | Glu | Tyr | Asn 400 |
| Pro | Gly | Gly | Asn | Phe 405 | Ile | Gly | Glu | Leu | Ile 410 | Tyr | Thr | Met | Gly | Asp 415 | Pro |
| Cys | Ser | Thr | Asp 420 | Glu | Asp | Cys | Gln | Cys 425 | Ala | Gly | Cys | Val | Cys 430 | Ser | Lys |
| Asp | Glu | Ala 435 | Leu | Cys | Ile | Ala | Pro 440 | | | | | | | | |